US005670361A

United States Patent [19]
Wong-Staal et al.

[11] Patent Number: 5,670,361
[45] Date of Patent: Sep. 23, 1997

[54] HIV-SPECIFIC RIBOZYMES

[75] Inventors: Flossie Wong-Staal; Mang Yu, both of San Diego, Calif.; Osamu Yamada, Kobe, Japan; Joshua O. Ojwang, Spring, Tex.; Markley C. Leavitt, La Jolla; Anthony Ho, San Diego, both of Calif.

[73] Assignee: The Regents of the University of California, Oakland, Calif.

[21] Appl. No.: 245,742

[22] Filed: May 17, 1994

Related U.S. Application Data

[63] Continuation-in-part of Ser. No. 62,465, May 17, 1993, abandoned.

[51] Int. Cl.$^6$ .......................... C12N 15/86; C12N 15/11; C12N 5/10
[52] U.S. Cl. .................. 435/240.2; 435/240.1; 435/320.1; 536/23.1
[58] Field of Search .................. 435/320.1, 240.1, 435/240.2; 424/93.2, 93.21; 536/23.1; 514/44

[56] References Cited

U.S. PATENT DOCUMENTS

| | | | |
|---|---|---|---|
| 4,987,071 | 1/1991 | Cech et al. | 435/91.31 |
| 5,037,746 | 8/1991 | Cech et al. | 435/91.31 |
| 5,093,246 | 3/1992 | Cech et al. | 435/6 |
| 5,116,742 | 5/1992 | Cech et al. | 435/91.31 |
| 5,144,019 | 9/1992 | Rossi et al. | 536/23.1 |
| 5,149,796 | 9/1992 | Rossi et al. | 536/23.2 |
| 5,168,053 | 12/1992 | Altman et al. | 514/44 |
| 5,180,818 | 1/1993 | Cech et al. | 536/23.1 |
| 5,254,678 | 10/1993 | Haseloff et al. | 536/23.2 |

FOREIGN PATENT DOCUMENTS

| | | |
|---|---|---|
| 0 360 257 | 3/1990 | European Pat. Off. . |
| WO90/13641 | 11/1990 | WIPO . |

OTHER PUBLICATIONS

Sullenger, et al., "Expression of Chimeric tRNA–Driven Antisense Transcripts Renders NIH 3T3 Cells Highly Resistant to Moloney Murine Leukemia Virus Replication," *Molecular and Cellular Biology* (Dec. 1990) 10(12): 6512–6523.

Biberfeld, et al., "HTLV–III Expression in Infected Lymph Nodes and Relevance to Pathogenesis of Lymphadenopathy" *AJP* 123:436–442 (1986).

Gartner et al., "The Role of Mononuclear Phagocytes in HTLV–III/LAV Infection" *Science* 233:215–219 (1986).

Mitsuya et al., "Molecular Targets for AIDS Therapy" *Science* 249:1533–1543 (1990).

Saiki et al., "Primer–Directed Enzymatic Amplification of DNA with a Thermostable DNA Polymerase" *Science* 239:487–491 (1988).

Ou et al., "DNA Amplification for Direct Detection of HIV–1 in DNA of Peripheral Blood Mononuclear Cells" *Science* 239:295–297 (1988).

Yamada et al., "Inhibition of Growth of HIV by Human Natural Interferon In Vitro" *Aids Research and Human Retroviruses* 4:287–294 (1988).

Haseloff and Gerlach, "Simple RNA enzymes with new and highly specific endoribonuclease activities" *Nature* 334:585–591 (1988).

Hampel and Tritz, "RNA Catalytic Properties of the Minimum (−)sTRSV Sequence" *Biochemistry* 28:4929–4933 (1989).

Baltimore, D., "Intracellular immunization" *Nature* 335:395–396 (1988).

Friedman et al., "Expression of a truncated virus trans–activator selectively impedes lytic infection by its cognate virus" *Nature* 335:452–454 (1988).

Freed et al., "A mutation in the human immunodeficiency virus type 1 transmembrane glycoprotein gp41 dominantly interferes with fusion and infectivity" *Proc. Natl. Acad. Sci. USA* 89:70–74 (1992).

Steffy and Wong–Staal, "Transdominant Inhibition of Wild–Type Human Immunodeficiency Virus Type 2 Replication by an Envelope Deletion Mutant" *J. of Virology* 67:1854–1859 (1993).

Sullenger et al., "Overexpression of TAR Sequences Renders Cells Resistant to Human Immunodeficiency Virus Replication" *Cell* 63:601–608 (1990).

Lisziewicz et al., "Tat–Regulated Production of Multimerized TAR RNA Inhibits HIV–1 Gene Expression" *The New Biologist* 3:82–89 (1991).

Edgington, Stephen M., ed. "Ribozymes' Patent History" *Bio/Technology* 11:624–625 (1993).

Alizon et al., "Genetic Variability of the AIDS Virus: Nucleotide Sequence Analysis of Two Isolates from African Patients"; *Cell* 46:63–74 (1986).

Cassel et al., "Retroviral–Mediated Gene Transfer into CD34–enriched Human Peripheral Blood Stem Cells"; *Exp. Hematology* 21:585–591 (1993).

Chang et al., "Ribozyme–Mediated Site–Specific Cleavage of the HIV–1 Genome"; *Clinical Biotechnology* 2(1): 23–31 (1990).

Culver et al., "Correction of ADA Deficiency in Human T Lymphocytes Using Retroviral–Mediated Gene Transfer"; *Transplantation Proceedings;* 23(1):170–171 (1991).

(List continued on next page.)

*Primary Examiner*—Mindy Fleisher
*Assistant Examiner*—Johnny F. Railey, II
*Attorney, Agent, or Firm*—Townsend and Townsend and Crew LLP

[57] ABSTRACT

This invention provides an infectious retrovirus having inserted between the 5' and 3' long terminal repeat sequences of the retrovirus a nucleic acid encoding an anti-HIV-type specific agent under the control of a pol III promoter. Host cells containing the retroviral vectors of this invention also are provided. Further provided are methods of interfering with or preventing HIV viral replication in a cell infected with HIV or likely to be infected with HIV.

13 Claims, 24 Drawing Sheets

OTHER PUBLICATIONS

Gurgo et al., "Short Communications—Envelope Sequences of Two New United States HIV-1 Isolates"; *Virology* 164:531–536 (1988).

Fauser A.A., "Long-Term Expression of Gene Introduction Into Normal Human T–Lymphocytes by Retroviral–Mediated Gene Transfer"; *Journal of Cellular Biochemistry* 45:353–358 (1991).

Forster and Symons, "Self–Cleavage of Plus and Minus RNAs of a Virusoid and a Structural Model for the Active Sites"; *Cell* 49:211–220 (1987).

Haas et al., "Successful Autologous Transplantation of Blood Stem Cells Mobilized with Recombinant Human Granulocyte–Macrophage Colony–Stimulating Factor"; *Exp. Hematology* 18:94–98 (1990).

Hampel, "'Hairpin' Catalytic RNA Model: Evidence for Helices and Sequence Requirement for Substrate RNA"; *Nucleic Acids Research* 18(2): 299–304 (1990).

Kikukawa et al., "Differential Susceptibility to the Acquired Immunodeficiency Syndrome Retrovirus in Cloned Cells of Human Leukemic T–Cell Line Molt–4"; *Journal of Virology* 57(3):1159–1162 (1986).

Korbling et al., "Autologous Transplantation of Blood–Derived Hemopoietic Stem Cells After Myeloablative Therapy in a Patient with Burkitt's Lymphoma"; *Blood* 67(2):529–532 (1986).

Lu et al., "High Efficiency Retroviral–Mediated Gene Transduction into CD34+ Cells Purified from Peripheral Blood of Breast Cancer Patients Primed with Chemotherapy and Granulocyte–Macrophage Colony–Stimulating Factor"; *Human Gene Therapy* 5:203–208 (1994).

Ratner et al., "Complete Nucleotide Sequences of Functional Clones of the AIDS Virus"; *AIDS Research and Human Retroviruses* 3:57–69 (1987).

Sanchez–Pescador et al., "Nucleotide Sequence and Expression of an AIDS–Associated Retrovirus (ARV–2)"; *Science* 227:484–491 (1985).

Starcich et al., "Characterization of Long Terminal Repeat Sequences of HTLV–III"; *Science;* 227:538–540 (1991).

Talbott et al., "Mapping the Determinants of Human Immunodeficiency Virus 2 for Infectivity, Replication Efficiency and Cytopathicity"; *Proc. Natl. Acad. Sci. USA* 90:4226–4230 (1988).

Walbot and Bruening, "Plant Development and Ribozymes for Pathogens"; *Nature* 334:196 (1988).

Ojwang et al., "Inhibition of human immunodeficiency virus type 1 expression by a hairpin ribozyme" *Proc. Natl. Acad. Sci. USA* 89:10802–10806 (1992).

Rossi et al., "The potential use of catalytic RNAs in therapy of HIV infection and other diseases" *Pharmac. Ther.* 50:245–254 (1991).

Koch and Ruprecht, "Animal models for anti–AIDS therapy" *Antiviral Research* 19:81–109 (1992).

Sarvar et al., "Ribozymes as Potential Anti–HIV–1 Therapeutic Agents" *Science* 247:1222–1225 (1990).

Lo et al., "Inhibition of Replication of HIV–1 by Retroviral Vectors Expressing tat–Antisense and Anti–tat Ribozyme RNA" *Virology* 190:176–183.

Miller, A. D., "Human gene therapy comes of age" *Nature* 357:455–460 (1992).

Herskowitz, I., "Functional inactivation of genes by dominant negative mutations" *Nature* 329:.

Joseph et al., "Substrate selection rules for the hairpin ribozyme determined by in vitro selection, mutation, and analysis of mismatched substrates" *Genes & Development* 7:130–138 (1993).

Cech and Bass, "Biological Catalysis by RNA" *Ann. Rev. Biochem.* 55:599–629 (1986).

Geiduschek, E.P., "Transcription by RNA polymerase III" *Ann. Rev. Biochem.* 57:873–914 (1988).

Arya et al., "Trans–Activator Gene of Human T–Lymphotropic Virus Type III (HTLV–III)" *Science* 229:69–73 (1985).

Jennings and Molloy, "Inhibition of SV40 replicon function by engineered antisense RNA transcribed by RNA polymerase III" *The EMBO Journal* 6:3043–3047 (1987).

Sullenger et al., "Expression of Chimeric tRNA–Driven Antisense Transcripts Renders NIH 3T3 Cells Highly Resistant to Moloney Murine Leukemia Virus Replication" *Molecular and Cellular Biology* 10:6512–6523 (1990).

Cotten and Birnstiel, "Ribozyme mediated destruction of RNA *in vivo*" 8:3861–3866 (1989).

Sarver et al., "Catalytic RNAs (Ribozymes): A New Frontier in Biomedical Applications" in: *AIDS Research Reviews*, eds. Koff, Wong–Staal & Kennedy (Marcel Dekker, Inc., New York) vol. 2, pp. 259–285 (1992).

Bass and Weintraub, "An Unwinding Activity that Covalently Modifies its Double–Stranded RNA Substrate" *Cell* 55:1089–1098 (1988).

Dropulić et al., "Functional Characterization of a U5 Ribozyme: Intracellular Suppression of Human Immunodeficiency Virus Type 1 Expression" *J. of Virology* 66:1432–1441 (1992).

Yamada et al., "A new method for extracting DNA or RNA for polymerase chain reaction" *J. of Virological Meths.* 27:203–210 (1990).

Chomczynski and Sacchi, "Single–Step Method of RNA Isolation by Acid Guanidinium Thiocyanate–Phenol–Chloroform Extraction" *Analytical Biochemistry* 162:156–159 (1987).

Embretson et al., "Massive covert infection of helper T lymphocytes and macrophages by HIV during the incubation period of AIDS" *Nature* 362:359–362 (1993).

Pantaleo et al., "HIV infection is active and progressive in lymphoid tissue during the clinically latent stage of disease" *Nature* 362:355–358 (1993).

Weerasinghe et al., "Resistance to Human Immunodeficiency Virus Type 1 (HIV–1) Infection in Human CD4+ Lymphocyte–Derived Cell Lines Conferred by Using Retroviral Vectors Expressing an HIV–1 RNA–Specific Ribozyme" *J. of Virology* 65:5531–5534 (1991).

Sioud and Drlica, "Prevention of human immunodeficiency virus type 1 integrase expression in *Escherichia coli* by a ribozyme" *Proc. Natl. Acad. Sci. USA* 88:7303–7307 (1991).

Chatterjee et al., "Dual–Target Inhibition of HIV–1 in Vitro by Means of an Adeno–Associated Virus Antisense Vector" *Science* 258:1485–1488 (1992).

Joshi et al., "Inhibition of Human Immunodeficiency Virus Type 1 Multiplication by Antisense and Sense RNA Expression" *J. of Virology* 65:5524–5530 (1991).

Rhodes and James, "Inhibition of human immunodeficiency virus replication in cell culture by endogenously synthesized antisense RNA" *J. of General Virology* 71:1965–1974 (1990).

Hope et al., "trans–Dominant Inhibition of Human Immunodeficiency Virus Type 1 Rev Occurs through Formation of Inactive Protein Complexes" *J. of Virology* 66:1849–1855 (1992).

Malim et al., "Functional Dissection of the HIV–1 Rev Trans–Activator—Derivation of a Trans–Dominant Repressor of Rev Function" *Cell* 58:205–214 (1989).

Lee et al., "Overexpression of RRE–Derived Sequences Inhibits HIV–1 Replication in CEM Cells" *The New Biologist* 4:66–74 (1992).

Trono et al., "HIV–1 Gag Mutants Can Dominantly Interfere with the Replication of the Wild–Type Virus" *Cell* 59:113–120 (1989).

"Report and Recommendations of the Panel to Assess the NIH Investment in Research on Gene Therapy," Orkin and Motulsky, Co–chairs, Dec. 7, 1995.

Johnston et al., Science 260:1286–1293 (1993).

Cournoyer et al., Annu. Rev. Immunol. 11:297–329 (1993).

Feinberg et al., AIDS Research and Human Retroviruses 8(6):1013–1022 (1992).

Poeschla et al., Current Opinion in Oncology 6:601–606 (1994).

Marshall, Science 269:1050–1055 (1995).

Zaia et al., Annals of the New York Academy of Sciences 660:95–106 (1992).

Yu et al., Proc. Natl. Acad. Sci. USA 92:699–703 (1995).

Yu et al., Virology 206:381–386 (1995).

Barinaga, Science 262:1512–1514 (1993).

RIBOZYME EFFECT ON TAT ACTIVITY

RIBOZYME EFFECT ON P24 EXPRESSION

| | | | | | |
|------|----|-----|-----|-----|-----|
| HXB2 | TG | CCC | GTC | TGT | TGT GT |
| MN   | TG | CCC | GTC | TGT | TaT GT |
| SF2  | TG | CCC | GTC | TGT | TGT GT |
| RF   | TG | CCC | GTC | TGT | TGT GT |
| HAN  | TG | CCC | GTC | TGT | TGT GT |
| ELI  | TG | CCC | GTC | TGT | TGT GT |
| Z2Z6 | TG | CCC | GTC | TGT | TGT GT |

*FIG. 3.*

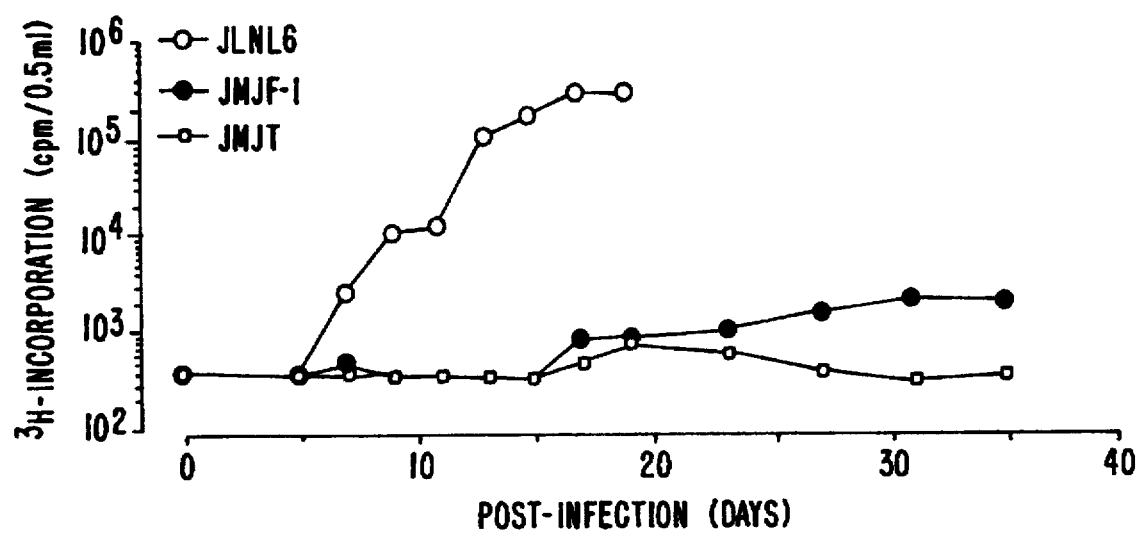
FIG. IIA.

HIV-SPECIFIC RIBOZYMES

This application is a continuation-in-part of U.S. Ser. No. 08/062,465, filed May 17, 1993 now abandoned, the contents of which are incorporated herein by reference.

The Government has rights in this invention pursuant to Contract No. DAMD 17-90-C-0094 awarded by the United States Army.

BACKGROUND OF THE INVENTION

AIDS, which is now known to be caused by the human immunodeficiency virus (HIV), has become a major threat to public health on a global scale. Preventing further spread of this disease is a major health priority in the United States and in many foreign countries. Although HIV was confirmed to be the causative agent of AIDS as early as 1984, few if any drugs or vaccines are publicly available which have been shown to treat or prevent AIDS. This is due, in large part, to the complexity of the causative agent itself.

HIV infects a variety of tissues and cells in the body. In addition, after entering a cell, the virus can "hide" in a cell of the central nervous system of a individual, some times for years, before symptoms of the disease appear.

Clinical progression in HIV-infected individuals is dependent upon continued virus expression via the recruitment of newly infected cells. Thus, some researchers believed that this etiological manifesation of viral propagation would provide the rationale for developing anti-HIV therapeutics. Indeed, nucleoside analogs which inhibit the viral reverse transcriptase have shown some clinical efficacy. However, the inherent toxicity of these drugs and the inevitable emergence of drug resistant HIV mutants in the course of treatment have removed this type of drug from serious consideration as an AIDS therapeutic. Accordingly, the search continues for novel, effective therapeutic regimens.

This invention provides a novel anti-HIV and thus, AIDS therapeutic that overcomes this limitation of present nucleotide-based therapies for AIDS prevention and treatment.

SUMMARY OF THE INVENTION

This invention provides an infectious retrovirus having inserted between the 5' and 3' long terminal repeat sequences of the retrovirus a nucleic acid encoding an anti-HIV-type specific agent under the control of a pol III promoter. Host cells containing the retroviral vectors of this invention also are provided. Further provided is a method of interfering with or preventing HIV viral replication in a cell infected with HIV. The method involves transducing the infected cell with a retroviral vector containing a nucleic acid encoding an anti-HIV-type specific agent under conditions favoring transduction of the vector and stable expression of the agent in the cell. Cells also may be transduced with the retroviral vector prior to HIV infection. When this is done, HIV infection can be prevented.

BRIEF DESCRIPTION OF THE DRAWINGS

FIG. 2A: HeLa cells transfected were harvested after 48 hours and subjected to CAT enzyme assay. The TLC slices were counted using scintillation counter and results expressed relative to the control. FIG. 2B: Supernatant was subjected to p24 antigen analysis and the values were represented as relative percentage of the control level. FIG. 2C: Total RNA was isolated using rapid isolation method (see Detailed Description of the Invention, infra). Twenty micrograms of total RNA were dotted and hybridized by [α-32p]UTP internally labeled HIV-1 specific probe. Lane 1: RNA prepared from pUC19/pHXB2gpt transfected cells and Lane 2: RNA from pJV-HR/pHXB2gpt transfected cells.

FIG. 3. Alignment of the target leader sequence of HIV-1 isolates (SEQ ID Nos. 6 through 12, respectively).

FIG. 4A: The effector plasmid (pSF-2) was co-transfected in duplicate or in triplicate into HeLa cells with the ribozyme containing retroviral vectors (0.5:10 µg, effector plasmid:ribozyme vector) pMJF-1, pMJT, pMJV, and pMHR (bars 1, 3, 4 and 5, respectively) or retroviral vector without ribozyme gene pLRNL-2 (bar 2). After 48 hours, the cells were harvested (see Detailed Description of the Invention, infra) and the supernatant was subjected to p24 antigen analysis. FIG. 4B: Total RNA was isolated from HeLa cells transfected with pMJF-1, pLRNL-2 (vector only), pMJT, pMJV, and pMHR and dotted on the membrane (see Detailed Description of the Invention, infra) and hybridized by 5'-end radiolabeled ribozyme specific probe. The intensity of the dots were quantified in scan units by phosphoroimager (Molecular Dynamics, California).

FIG. 5A: For HIV-1 pEli, 0.25:10 µg (effector plasmid:ribozyme vector) were co-transfected. FIG. 5B: For HIV-1 pMN, 0.25:10 µg (effector plasmid:ribozyme vector) were co-transfected. After 48 hours the cells were harvested (see Detailed Description of the Invention, infra) and the supernatant was subjected to p24 antigen analysis.

Methods 27:203 (1990), incorporated herein by reference, except that the extraction step with glass powder was omitted. After the PCR with and without reverse transcription, 10 μl of each amplified product was subjected to electrophoresis on a 3% low melting agarose gels (Boehringer) in Tris-borate buffer (pH 7.2) and Southern blot analysis was performed with [$^{32}$P]-end labeled Rib 3 (5'-CAA, CCA, GAG, AAA, CAC, ACG, TT-3') (SEQ ID NO. 3). The expression of the ribozyme in uninfected MLNL6 (without the ribozyme), MMJF-1, MMJT, JLNL6 (without the ribozyme), JMJF-1 and JMJT cells was shown. A retroviral vector plasmid (pMJT) containing the ribozyme was used as a positive control of the ribozyme DNA. 246 —RT:PCR was performed without reverse transcriptase. The size of the amplified product is 54 bp.

Figure 7:
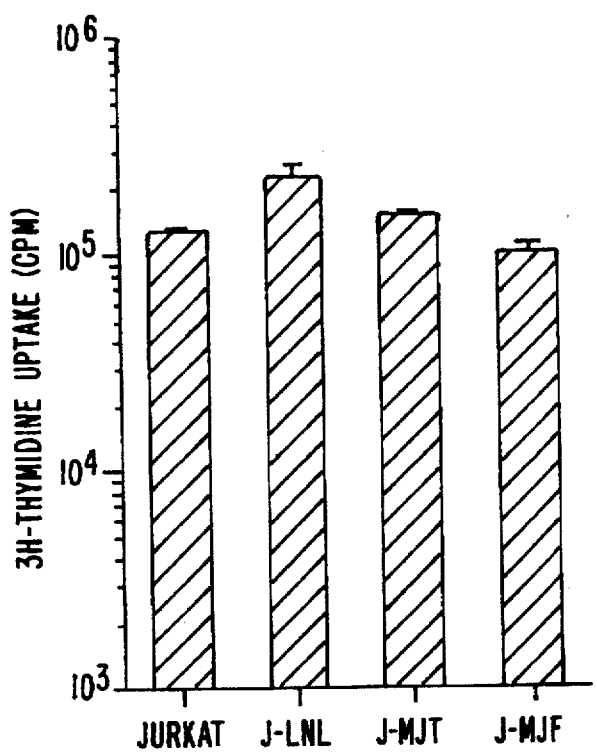

FIG. 7 shows proliferation of Jurkat cells expressing the HIV-1 specific ribozyme. Parental Jurkat cells (Jurkat Clone 3.8) and test cell lines were split into quadruplicate wells of a U-bottomed 96 well plate at $10^4$ cells/100 μl/well. One hundred μl of RPMI 1640 supplemented with 10% FBS containing 1 μCi of [$^3$H]-(methyl)thymidine (NET-027, NEN) was added to each well. After 48 hours, the cells were harvested on filter paper. Radioactivity of the filter was measured in scintillation spectrometer (Beckman). The data are shown as mean ±S.D. (n=4).

FIG. 8. Inhibition of expression of p24 antigen from diverse HIV-1 strains by the HIV-1 specific ribozyme. HIV-1 strains HXB2, MN, Eli or J677-2 (an uncloned clinical isolate) were used to infect Jurkat cells expressing the ribozyme (JMJF-1 and JMJT cells) and control Jurkat cells transduced by the retroviral vector without the ribozyme (JLNL6 cells) at the input M.O.I. of 0.01 (or 0.1 for the slower growing strain J677-2). J677-2 was passaged once in MT-4 cells after isolation by cocultivation of PBMC from an AIDS patient and normal PBMC. ○ JLNL6, ● JMJF-1, □ JMJT FIG. 9. Lack of inhibition of HIV-2 replication by the HIV-1 specific ribozyme. HIV-1 HXB2 or HIV-2 KR was infected into Molt-4/8 cells expressing the ribozyme (MMJF-1 and MMJT) and Molt-4/8 cells transduced by the retroviral vector without the ribozyme (MLNL6) at the input M.O.I. of 0.01 (HXB2) or 0.001 for the faster growing strain HIV-2 KR. ○ MLNL6, ● MMJF-1, □ MMJT. Infectious titer (TCID$_{50}$) of virus preparations of these virus strains was determined using MT-2 cells by the method of Yamada, O. et al. *AIDS Res. Hum. Retroviruses* 4:287 (1988), incorporated herein by reference. The cells were washed twice with RPMI1640 medium after virus-adsorption for 2 hours and resuspended in RPMI 1640 medium supplemented with 10% FBS at the concentration of $10^5$ cells/ml. These infected cells were cultured for 6 days. Small aliquots of the culture fluid were collected at every 2 days and the level of p24 or p26 antigen was determined by HIV-1 or SIV/HIV-2 antigen capture ELISA test (Coulter).

Figure 10:
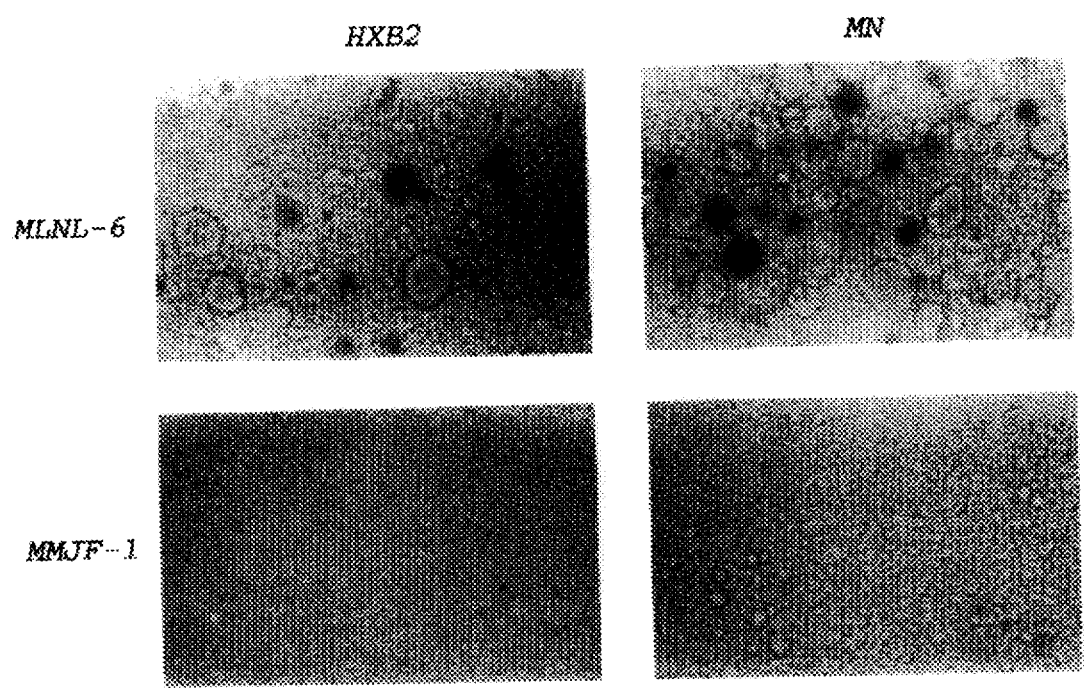

FIG. 10. Syncitia formation in MLNL6 and MMJF-1 cells on day 9 after infection. HIV-1 HXB2 or MN strain was used to infect Molt4/8 cells expressing the ribozyme (MLNL6 and MMJF-1) at input M.O.I. of 0.01. The cells were washed twice with RPMI 1640 medium after virus-adsorption for 2 hours and resuspended in RPMI 1640 medium supplemented with 10% FBS at the concentration of $10^5$ cells/ml. The cells were divided at every 2 days to make the concentration of $3\times10^5$ cells/ml since day 5 after infection.

Figure 11B:
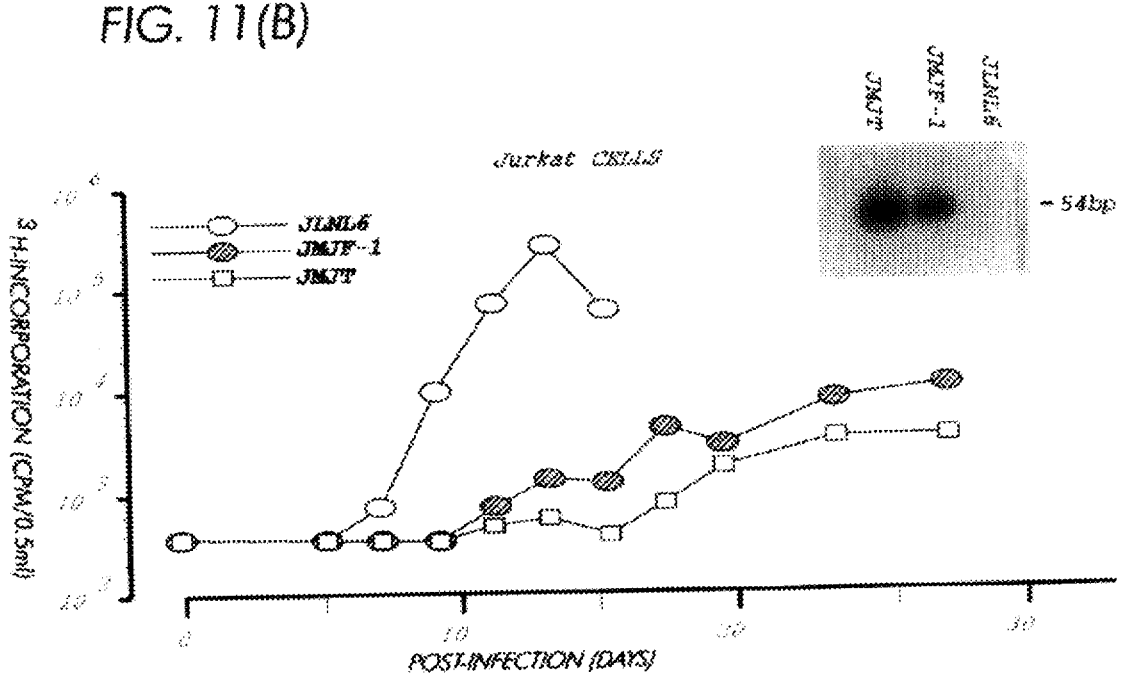

FIGS. 11A and 11B. Inhibition of RT activity in HIV-1/HXB2 or HIV-1/MN-infected Jurkat cells expressing the HIV-1 specific ribozyme in long term culture. HIV-1 HXB2 (A) or MN (B) was infected into JLNL6, JMJF-1 and JMJT cells at the input M.O.I. of 0.01 respectively. The cells were washed twice with RPMI 1640 after virus-adsorption for 2 hours and resuspended in RPMI 1640 supplemented with 10% PBS at the concentration of $10^5$ cells/ml. At day 5 and thereafter, the cells were divided at every 2 days to maintain $3\times10^5$ cells/ml. The culture supernatants were tested for the presence of HIV RT activity. Briefly, 0.5 ml duplicate aliquots of the supernatants were mixed with 0.24 ml of 30% polyethylene glycol 6000 and 20 ml of 4M NaCl. After microcentrifugation at 14000 rpm for 30 minutes, the supernatants were removed and 10 ml each of TNE solution (10 mM Tris-HCl pH 7,8; 100 mM NaCl; 1 mM EDTA) as added to the tubes. After mixing, 40 ml of a mixture containing 250 mM of Tris-HCl pH 7.8; 250 mM MgCl$_2$; 250 mM KCl; 25 mM dithiothreitol; 1.25 mg/40 ml of poly(rA) p(dT)12-18 (Pharmacia); 2.5 mCi/0.25 nmol/40 ml of [$^3$H] dTTP (NEN) was added and incubated at 37° C. for 1 hour. Ten ml of 0.2M EDTA was added. A sample (50 ml) of the mixture was then spotted onto DE81 paper (whatman), air-dried, washed five times with 5% Sodium pyrophosphate and twice more with water. The paper was then dried, and the radioactivity was measured in a scintillation spectrometer (Beckman). No radioactivity was detected when poly(dA)poly(dT) was used instead of poly (rA)poly(dT). ○ JLNL6, ● JMJF-1, □ JMJT FIG. 11 (inset). HIV-1 specific ribozyme expression in the stable cell lines after infection. The ribozyme expression in Jurkat cells JMJT and JMJF-1 on day 23 after infection with HIV-1/MN was examined by the RT PCR as described in FIG. 6. Uninfected JLNL6 cells were used as negative control. The PCR without reverse transcription was also performed and no amplified product was detected.

Figure 12A:
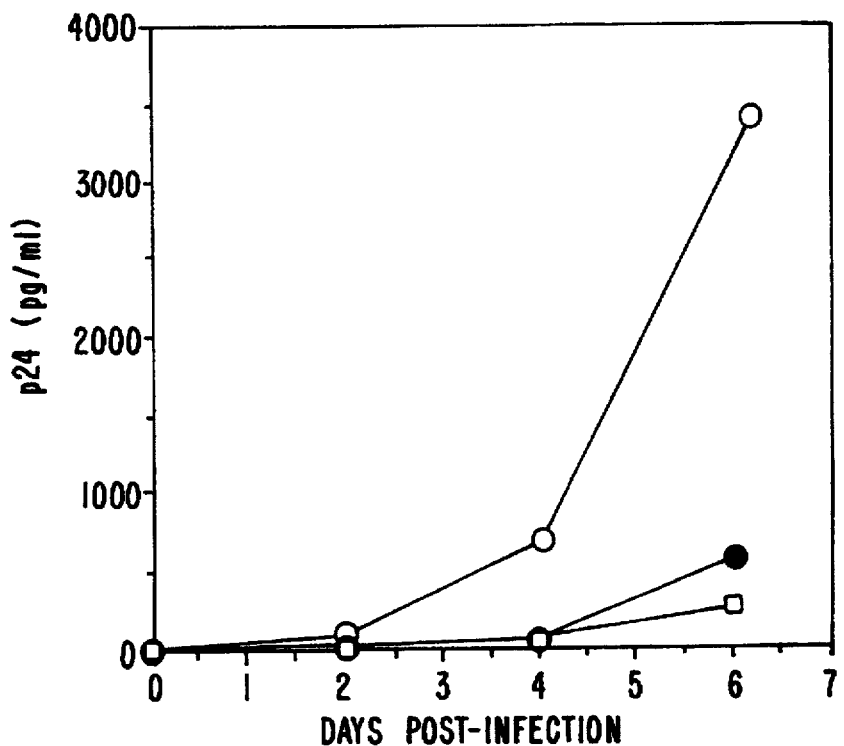
Figure 12B:
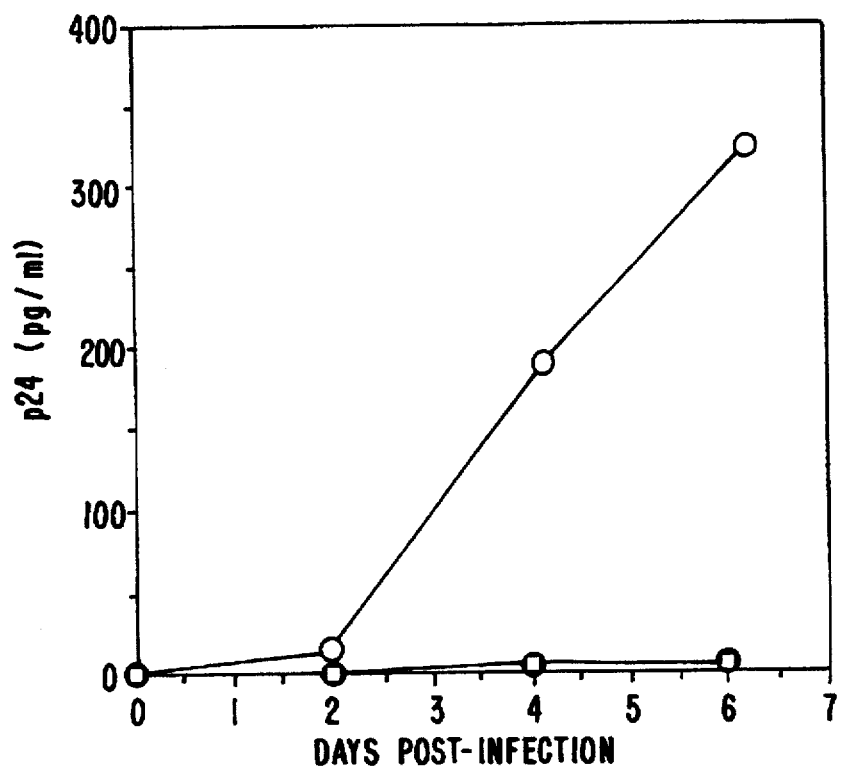
Figure 13:
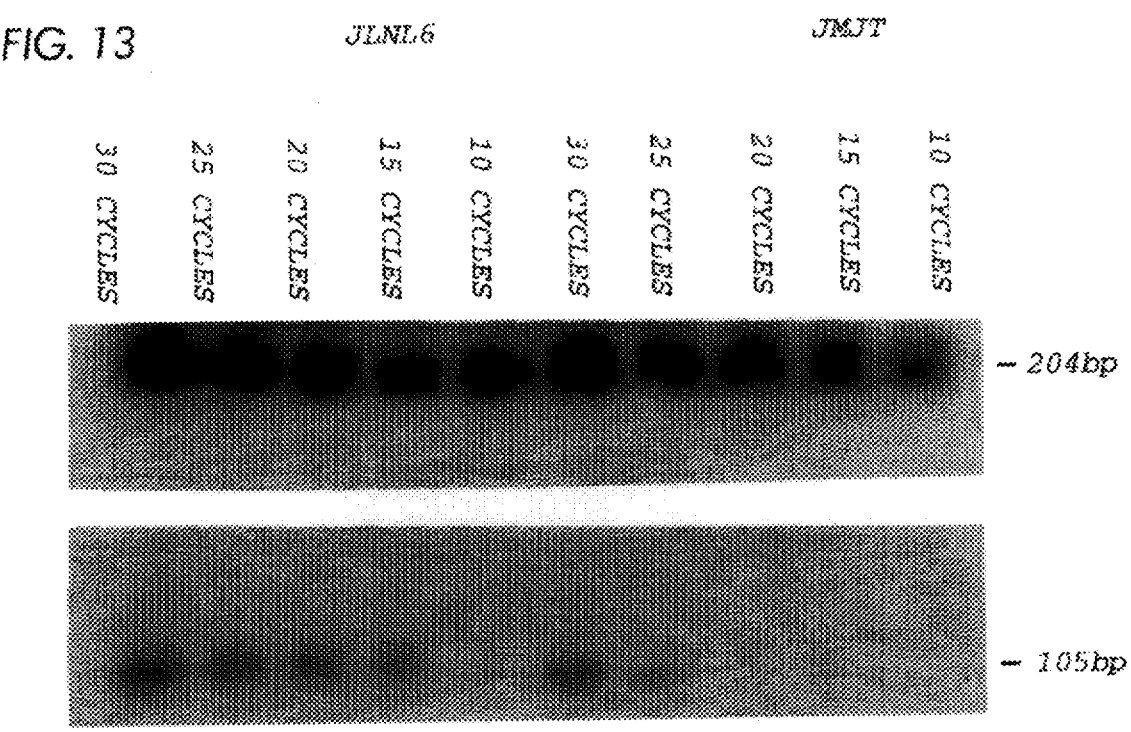

FIG. 12. Rechallenge of Jurkat cells expressing the HIV-1 specific ribozyme with "escape" virus. The culture supernatant of JMJF-1 cells infected with HIV-1 HXB2 or MN strains collected on day 35 or day 23, respectively, in the experiment shown in FIG. 11 was used to reinfect the JLNL6, JMJF-1 and JMJT cells. The input M.O.I. was 0.0004 and 0.01 in HXB2 and MN, respectively. Since the infectivity of HXB2 collected on day 35 was very low, input M.O.I. could not be adjusted to 0.01. The level of p24 was determined by HIV-1 antigen capture ELISA test (Coulter). ○ JLNL6, ● JMJF-1, □ JMJT FIG. 13. Effect of the HIV-1 specific ribozyme on proviral DNA synthesis in JMJT cells early after infection with HIV-1. HIV-1 proviral DNA level at the early stage of the infection with HXB2 in JLNL6 and JMJT cells was determined semi-quantitatively by the nested double PCR. Cellular genomic DNA was extracted from JLNL6 and JMJT cells 18 hours after infection with HIV-1 HXB2 by the method using proteinase K and phenol/chloroform. One μg each of the DNA extract was used as template for the 1st PCR. The composition of the reaction mixture for both first and second PCR was 50 mM Tris (pH 8.3); 6 mM MgCl$_2$; 40 mM KCl; 1 mM dithiothreitol; 200 mM each of dATP, dGTP, dTTP and dCTP; 2.5 units of Taq polymerase; and 1 mM each of primers (Promega). Primer pairs for HIV-1 LTR were used for the amplification of HIV-1 DNA (the amplified product includes the target sequence to the ribozyme). First PCR was carried out (94° C. for 1 minute, 54° C. for 1 minute, 72° C. for 1 minute: 30 cycles) with a primer pair SK29 and GK2 (5-CGG, CGG, ATC, CCG, GGC, GCT, TCA, GCA, AGC, CGA-3') (SEQ ID No. 4). A primer pair for β-globin which is PC03/GH21 for internal control, was added to the same reaction tubes at the time point after 10th cycle of the first PCR. For the second PCR, 1/10th volume of the first PCR product was added and the amplification was carried out (30 cycles) with primer pairs of SK29/SK30, Ou, C-Y. et al., *Science* 239:295 (1988) incorporated herein by reference and RS06 (see Saiki, R. et al. *Science* 239:487 (1988) incorporated herein by reference)/GH21. Ten μl each of the second PCR product was collected at every 5 cycles and the amplified product was detected by gel-electrophoresis and Southern blot analysis. Southern blot analysis was performed separately by hybridization with [$^{32}$P]-end labeled SK31 (see Ou, C-Y et al., supra incorporated herein by reference) or RS06 for HIV-1 or β-globin DNA, respectively. The size of amplified product specifically for HIV-1 is 105 basepairs and for β-globin is 204 basepairs. The results of detection of the amplified products collected at different cycles are shown.

Figure 14:
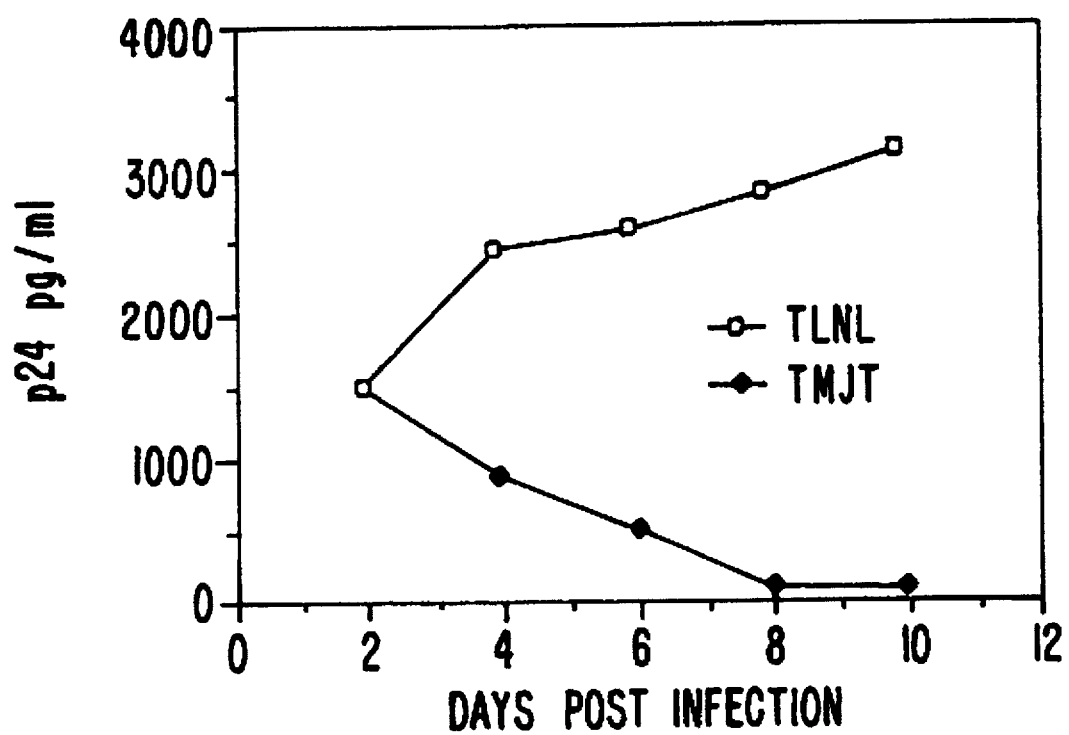

FIG. 14. HIV-1 challenge of transduced/selected human peripheral blood lymphocytes. Human PBMCs were isolated from blood by Ficoll-Hypaque centrifugation and plated at a density of $1 \times 10^6$ cells ml in RPMI media with 10% fetal calf serum, 5 μg/ml PHA-P and 20 U/ml IL-2. After 2 days incubation at 37° C., cells were centrifuged and washed prior to transduction. Filtered supernatants from PALNL-6 or PAMJT packaging cell lines were incubated at 37° C. for 4–6 hours with $3 \times 10^6$ stimulated PBMCs in the presence of 4 μg/ml polybrene. The PBMCs were washed and cultured overnight in RPMI+10% FCS, 20 U/ml IL-2 at a density of $1 \times 10^6$/ml. The transduction procedure was repeated daily for 3 days. Cells were selected in RPMI+10% FCS, 20 U/ml IL-2 with 400 μg/ml G418 for 8 days followed by 3 days culture without G418. Control cells which had not been exposed to packaging line supernatant did not survive this procedure as determined by trypan blue dye exclusion. Selected cells ($2 \times 10^5$) were infected for 2 hours (M.O.I.= 0.01), washed once and plated in RPMI+10% FCS, 20 U/ml IL-2 at $1 \times 10_6$/ml. Half of the culture media was harvested and replaced with fresh media every 2 days. Viral production was monitored by antigen capture (p24) ELISA (Coulter). LNL-6 and MJT transduced/selected cell lines are designated TLNL and TMJT respectively.

Figure 15A:
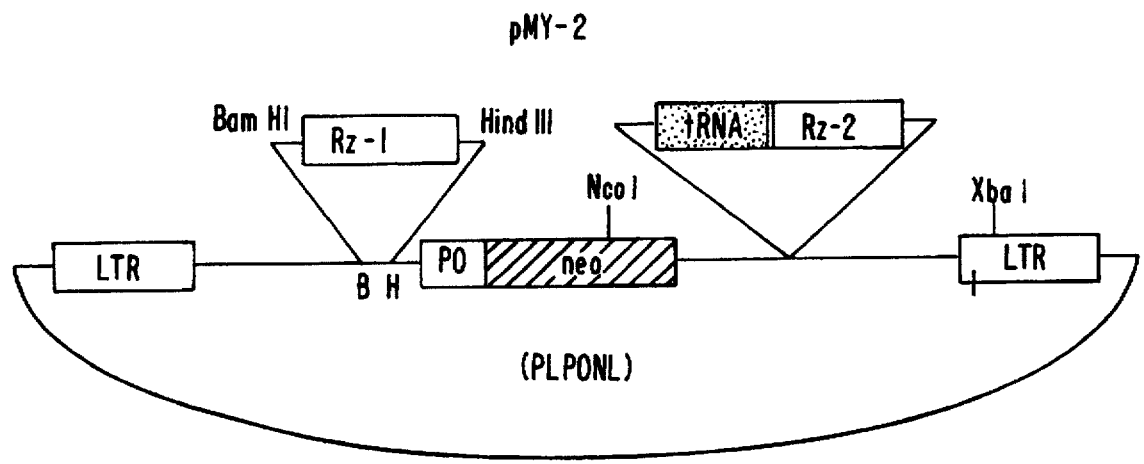
Figure 15B:
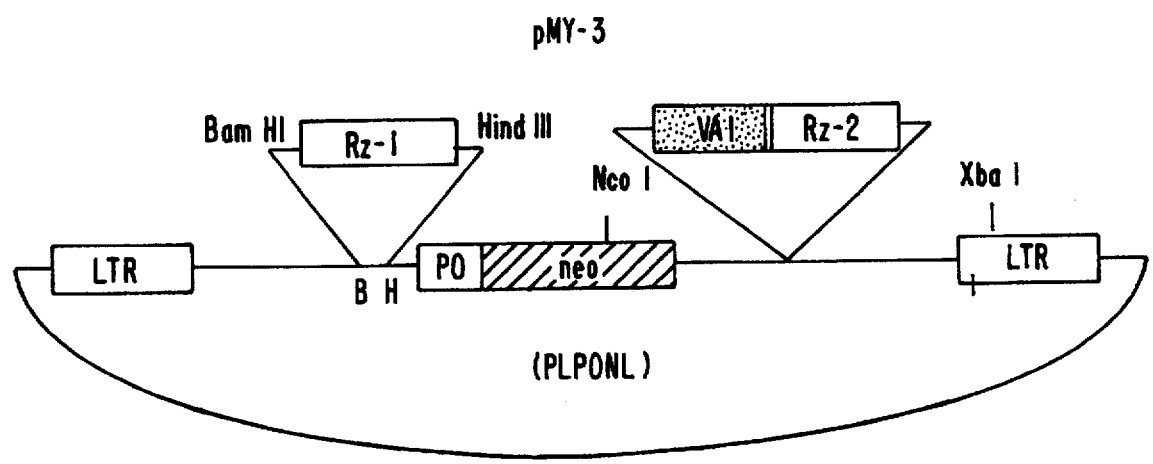

FIG. 15. Schematic representation of the retroviral vector constructions expressing multi-target ribozymes (not drawn to scale). See Detailed Description of the Invention for detail.

Figure 16A:
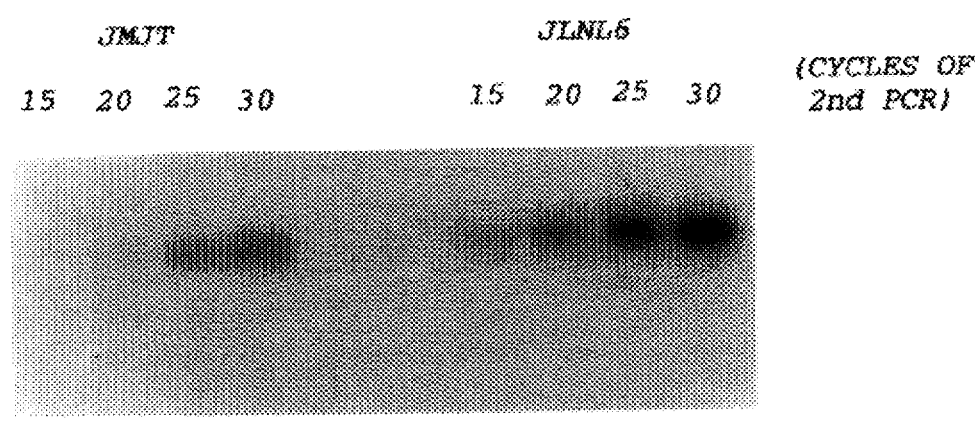
Figure 16B:
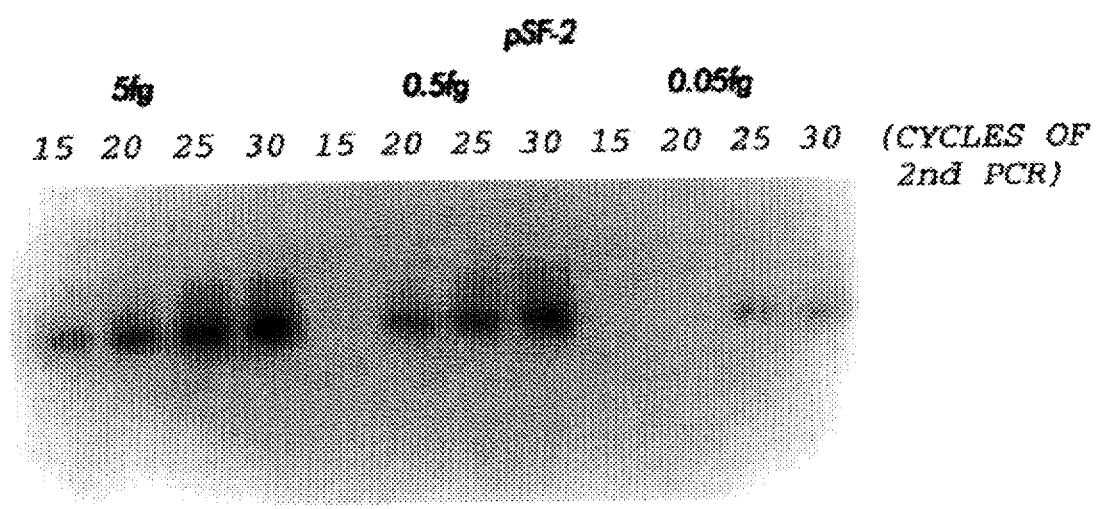

FIG. 16. Effect of the ribozyme on proviral DNA synthesis in JMJT cells at the early stage of infection with HIV-1 HXB2. HIV-1 proviral DNA levels 6 hours after infection with HXB2 in JLNL6 and JMJT cells were determined semi-quantitatively by nested double PCR. The results of detection of the amplified products collected at 15, 20, 25 and 30 cycles on the second PCR were shown. Different amounts (0.05–5 fg) of pSF-2 were amplified using the same primers and conditions (see infra) to estimate the relative amounts of HIV-1 DNA.

Figure 17:
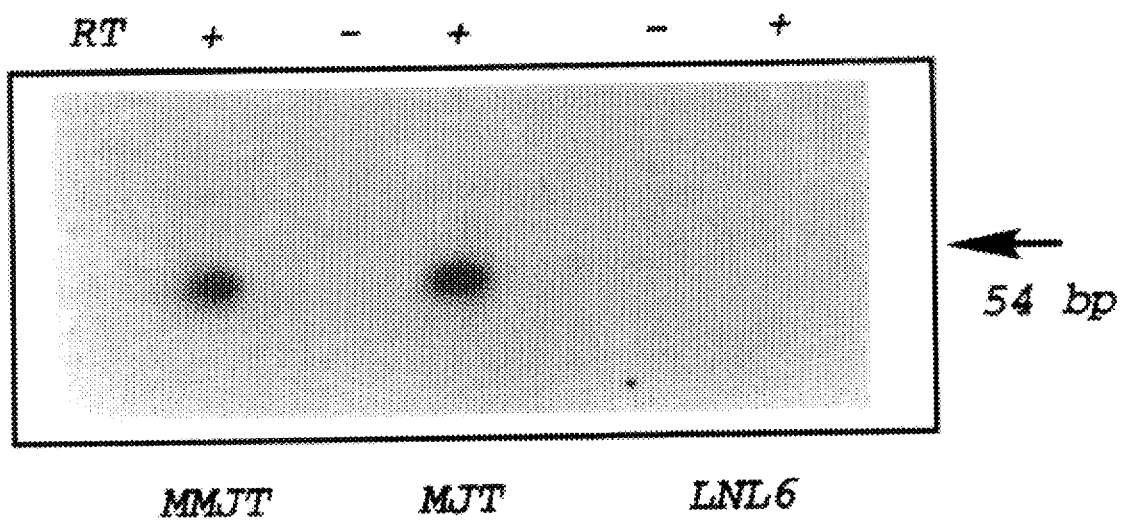

FIG. 17. Southern blot analysis of RT-PCR products from transduced/selected cultures. − and + indicate presence of reverse transcriptase in the RT-PCR reaction. RNAs are isolated from: MMJT, Molt4/clone 8 stably transduced with MJT; MJT and LNL, PBMCs transduced with either MJT or LNL-6, selected in G418 containing media for 8 days and subsequently cultured for 1 week without G418.

Figure 18A:
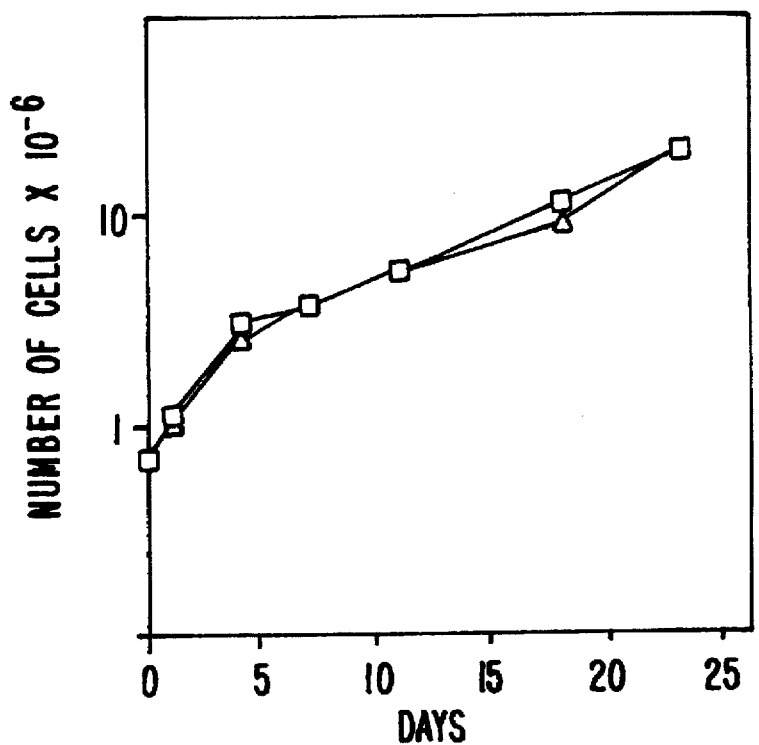
Figure 18B:
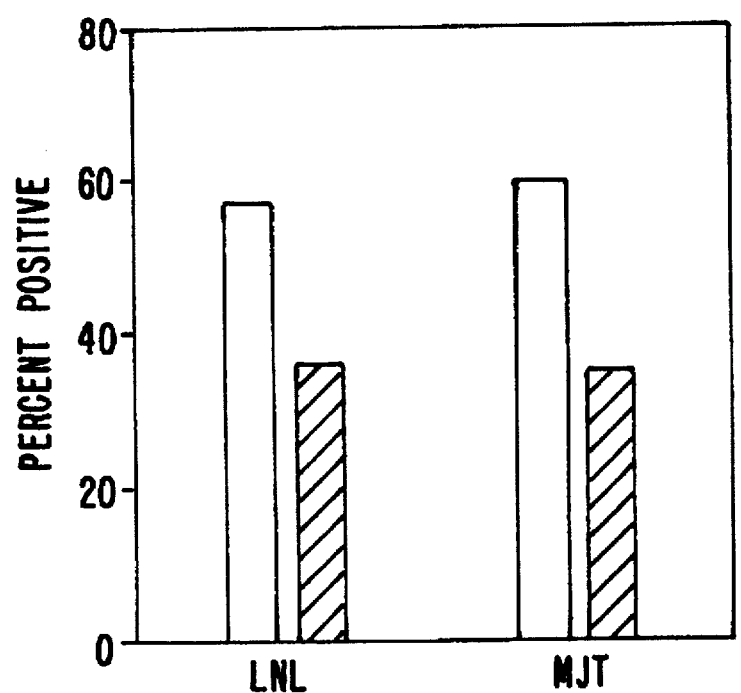

FIGS. 18A and 18B. Growth and CD4/CD8 characteristics of selected cultures (donor 054). A: Growth of LNL-6Δ, and MJT☐ transduced cultures after G418 selection. B: Percentage of CD4+☐, and CD8+■ cells after selection as determined by FACS.

FIGS. 19A to 19D. Challenge of transduced/selected cultures with HIV-1 and HIV-2. A, C: HIV-1HXB2 and B: HIV-2KR viral production in transducted/selected cultures; LNL-6Δ, MJT☐. Cultures in panels A and B (donor 054) were infected in parallel with HIV-1 or HIV-2. Panel C represents long-term HIV-1 challenge of transduced/selected cultures from donor 029. D: Clinical HIV-1 isolate production in transduced/selected cultures. Donor 052+ clinical isolate F (LNL-6Δ, and MJT☐); donor 061+clinical isolate G (LNL-6▲, and MJT☐).

Figure 20A:
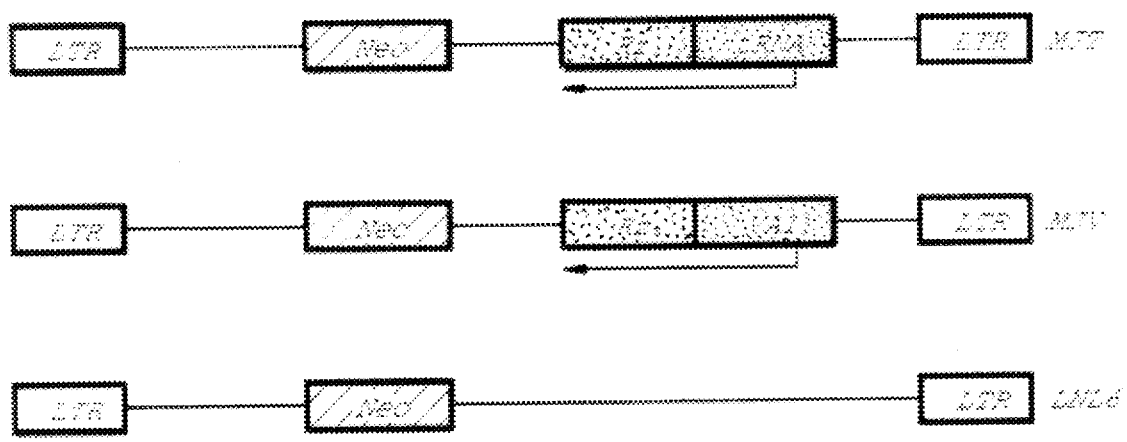
Figure 20B:
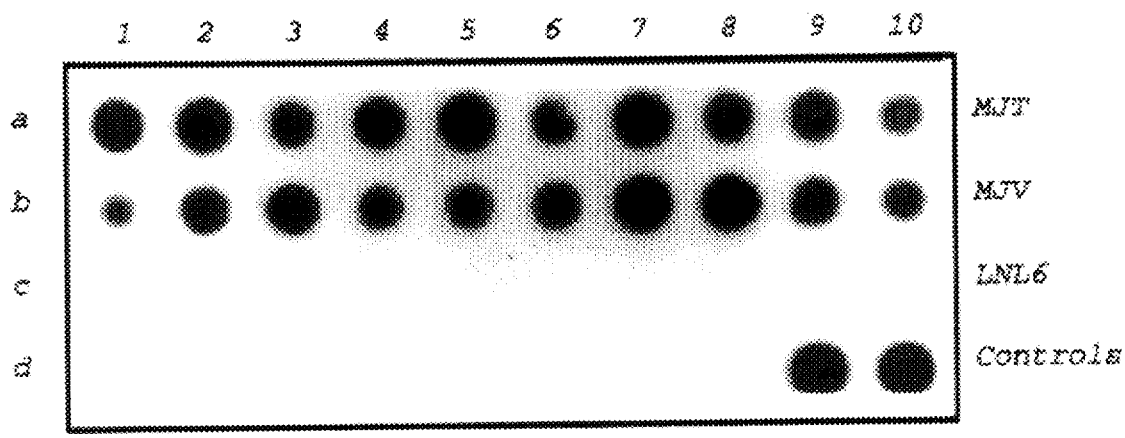

FIGS. 20A and 20B. A: Schematic representation of the retroviral vector constructions. The vectors in which the ribozyme was driven by internal pol III promoters were constructed as follows: the fragment containing the human tRNA$_{val}$ or adenovirus VA1 pol III promoter-ribozyme cassette (including the termination signal) (see Ojwang et al. *P.N.A.S.*, U.S.A. 89:10809 (1992), incorporated herein by reference) was inserted into the retroviral vector pLNL6 at the Hind III site, downstream of the neo gene as indicated. The resulting retroviral vectors were designated pMJT (the one with tRNA promoter) and pMJV (the one with VA1 promoter). The retroviral vectors were packaged by the standard method using an ecotropic cell line, psi2, and an amphotropic cell line, PA317. The titers of all three vectors were determined to be approximately $10^5$ CFU/ml using 208F cells. B: Ribozyme expression assay by RNA PCR. Total RNA from 10 colonies of each sample were extracted by the acid guanidinum thiocyanate-phenol/chloroform extraction method. 0.1 μg of the total RNA after treatment with deoxyribonuclease I (RQ1 DNase; Promega) was used as the template for reverse transcription (RT). Polymerase chain reaction (PCR), combined with RT, was carried out (94° C. for 1 minute, 45° C. for 1 minute, 72° C. for 1 minute; 30 cycles) with a primer pair of Rib 4(5'-CAC, ACA, ACA, AGA, AGG-3') (SEQ ID NO. 1) and Rib 2 (5'-TAC, CAG, GTA, ATA, TAC, CAC-3') (SEQ ID NO. 2). After PCR with or without RT, 10 μl of each amplified product was subjected to a dot blot assay. Hybridization was performed with [$^{32}$P]-end labeled 3rd oligonucleotides Rib 3, (5' -CAA, CCA, GAG, AAA, CAC ACG, TT-3' (SEQ ID No. 3), derived from the internal sequence of the ribozyme). a=MJT, b=MJV, c=LNL6. d=miscellaneous controls: d1 and d2, untransduced stem/progenitor cells; d3, combination of b1–b5 (without RT); d4, combination of b6–b10 (without RT); b5, combination of a1–a5 (without RT); d6, combination of a6–a10 (without RT). d9 and d10, $2 \times 10^3$ MJT transduced Jurkat T-cell, as the positive controls.

Figure 21:
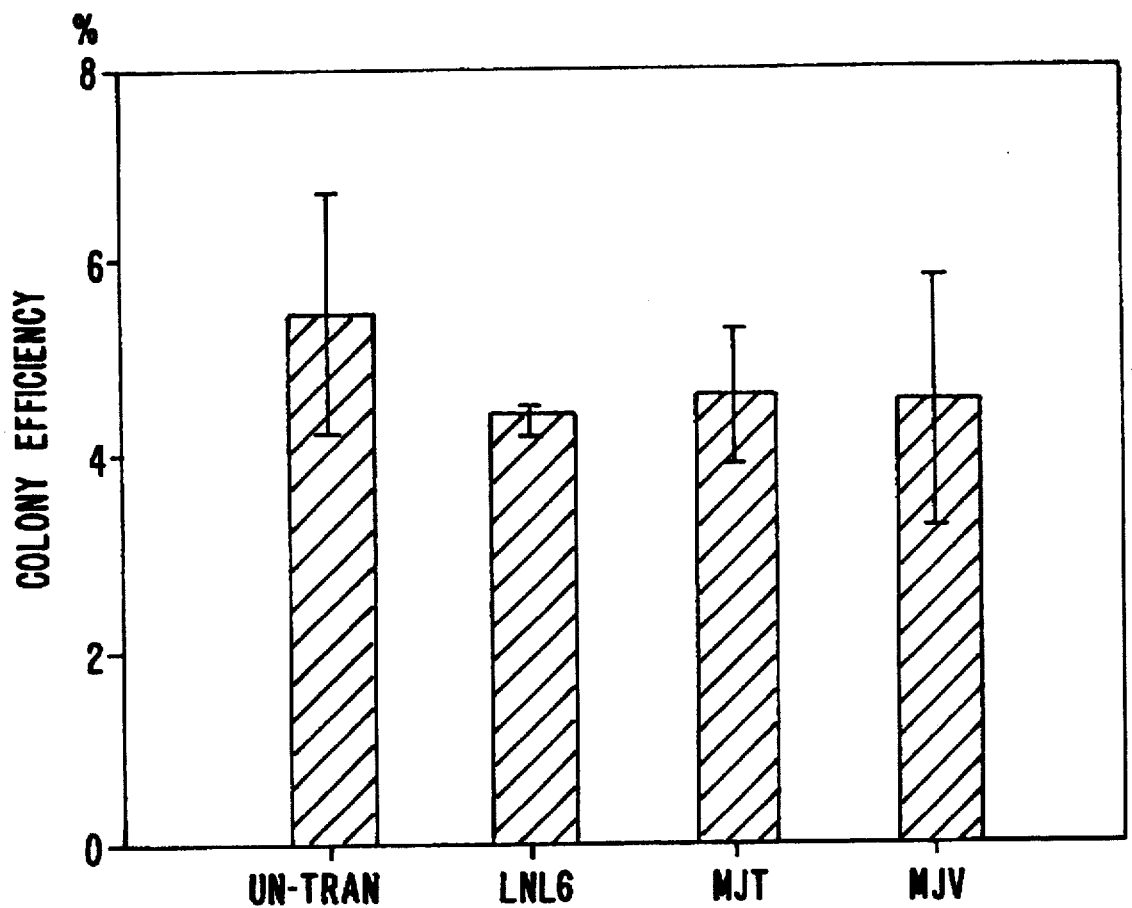

FIG. 21. Comparison of colony efficiency of the retroviral vector-transduced stem/progenitor cells. Colony efficiency was calculated by dividing the total number of colonies formed (the numbers at the bottom of the TABLE II) by the number of stem cells plated (5000). The error bars represent the variation of the colony numbers obtained from the three experiments using stem/progenitor cells isolated from cord blood of independent donors.

Figure 22A:
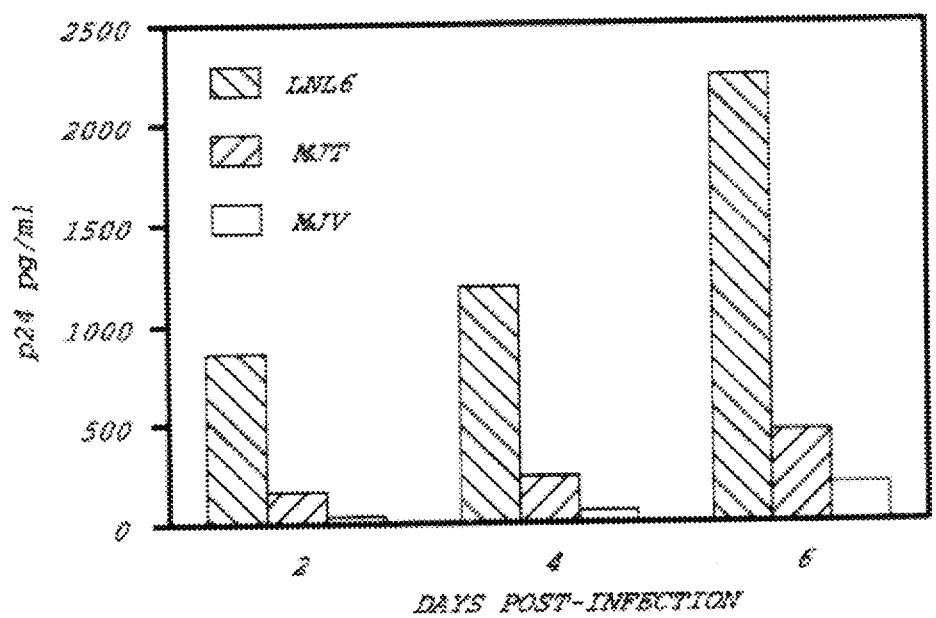
Figure 22B:
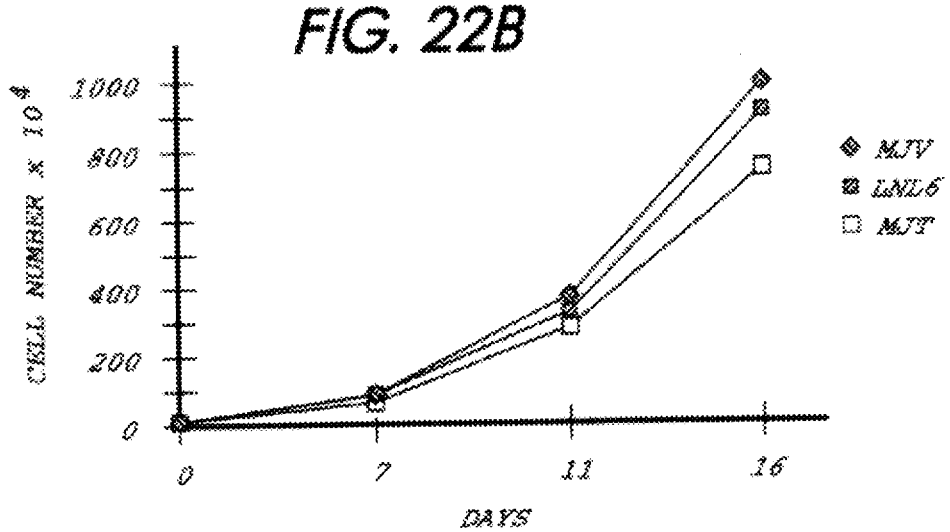
Figure 22C:
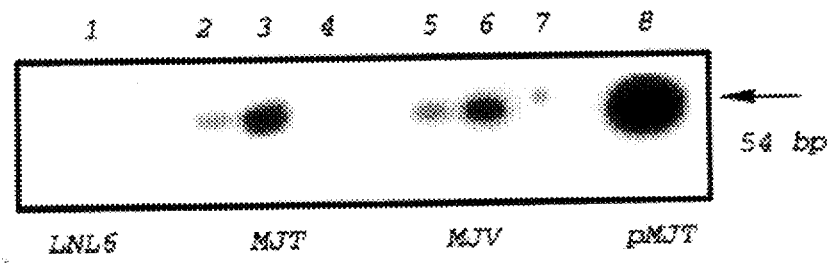

FIGS. 22A to 22C. A: Inhibition of HIV-1 replication by the ribozyme in macrophage cells derived from stem cells. The transduced stem/progenitor cells were maintained in 15 ml culture tubes (delta culture) with IMDM IL-3, IL-6, SCF for 3 weeks. Cultures were then placed on human sera coated plates (Costar 24 well #3524) for 2–4 hours and non-adherent cells were removed. Cultures were thereafter maintained in RPMI medium with 10% FCS, 10% normal human serum, and GM-CSF (1 ng/ml). After an additional 3 to 4 weeks, macrophage/monocytes derived from the stem cells under growth conditions were challenged using the macrophage tropic strain HIV-1/Bal. Cell culture supernatants were collected at time points indicated, and the standard HIV p24 ELISA were performed. B: Growth curves of the transduced stem cells. LNL6, MJT and MJV retrovirus-transduced stem cells were cultured under the conditions described in the legend A of this Figure. Total cell numbers were counted at the different time points indicated. 0.4% Trypan-Blue (GIBCO BRL) was used to exclude any dead cells from being counted under the microscope. C: Long term ribozyme expression in macrophages derived from transduced stem cells. Total RNA from each sample of about $10^4$ macrophage cells (about 2 months after stem cell transduction) was extracted by the acid guanidinum thiocyanate-phenol/chloroform extraction method. 0.1 μg of the total RNA was used as the template for reverse transcription (RT), in the presence of either Rib 4 (LTR transcript-specific, lanes 2 and 5) or Rib 2 (pol III transcript-specific, lanes 3 and 6). PCR was carried out by adding the second primer under the reaction conditions described in FIG. 1B. After the PCR with (lanes 1, 2, 3, 5, and 6) or without RT (lanes 4 and 7), 10 μl (10%) of each amplified product was subjected to electrophoresis on a 3% low-melting-point agarose gel (Boehringer) in Tris-borate buffer (pH 7.2), and Southern blot analysis was performed using a [$^{32}$P]-end labeled 3rd probe Rib 3, derived from the internal sequence of the ribozyme. Lanes 2, 3, 4=MJT; Lanes 5, 6, 7=MJV, Lane 1=LNL-6, Lane 8 is a positive ribozyme size control of DNA PCR product using the plasmid pMJT as the template. In all the control lanes (1, 4, 7, and 8), both Rib 2 and Rib 4 primers were added at the same time in the reverse transcription step.

DETAILED DESCRIPTION OF THE INVENTION

Gene therapy is an exciting new modality for treatment of human diseases. In addition to correction of genetic defects by insertion of functional cellular genes, gene therapy can also aim to stimulate immune response against tumor or viral infected cells, or to inhibit expression/function of infectious, pathogenic agents.

Since the identification of human immunodeficiency virus (HIV) as the causative agent for acquired immune deficiency syndrome (AIDS), there has been a concerted effort to develop strategies which inhibit virus replication. In theory, inhibition of HIV replication should be achievable by interfering with various key steps in the viral life cycle, including virus entry, reverse transcription, integration, transcription, RNA processing, transactivation, translation, packaging, and release of virus particles. Indeed, the life cycle of HIV provides many attractive steps for potential intervention by gene therapy, including introducing into HIV infected cells transdominant mutant gag and envelope genes which would interfere with HIV virus entry, TAR decoys to inhibit transcription and trans-activation of HIV, RRE decoys and transdominant REV mutants to inhibit HIV RNA processing, to give a few examples.

Antisense (RNA or DNA) nucleotides have been used to target and prohibit the utilization of viral mRNA in the HIV-1 life cycle. However, the stoichiometric nature of antisense inhibition imposes limits on this approach to inhibition of intracellular HIV infection and replication.

HIV-type specific ribozymes are shown herein to overcome the limitations of traditional antisense technology to thwart HIV infection and replication in cells. Ribozymes are RNA molecules that posses RNA catalytic activity. A catalytic stand cleaves a specific site in target RNAs; the number of cleaved RNAs is greater than what has been predicted based on stoichiometry.

As used herein, "ribozymes" are intended to include RNA molecules that contain anti-sense sequences for specific recognition, and a RNA-cleaving enzymatic activity. The catalytic strand cleaves a specific site in a target RNA at greater than stoichiometric concentration. Two "types" of ribozymes are particularly useful in this invention, the hammerhead ribozyme (Rossie, J. J. et al., Pharmac. Ther. 50:245–254 (1991) incorporated herein by reference) and the hairpin ribozyme. (Hampel et al., Nucl. Acids Res. 18:299–304 (1990) and U.S. Pat. No. 5,254,678, issued Oct. 19, 1993, each incorporated herein by reference.) Because both hammerhead and hairpin ribozymes are catalytic molecules having antisense and endoribonucleotidase activity, ribozyme technology has emerged as a potentially powerful extension of the antisense approach to gene inactivation. As will be shown in detail below, intracellular expression of hammerhead ribozymes and a hairpin ribozyme directed against HIV-1 RNA has been shown to confer significant resistance to HIV-1 infection.

This ribozyme can be a hammerhead (for example, as described by Forster and Symons (1987) Cell 48:211–220; Haseloff and Gerlach (1988) Nature 328:596–600; Walbot and Bruening (1988) Nature 334:196; Haseloff and Gerlach (1988) Nature 334:585, each incorporated herein by reference) or a hairpin ribozyme (for example, as described by Haseloff et al., U.S. Pat. No. 5,254,678, issued Oct. 19, 1993 and Hempel et al., European Patent Publication No. 0 360 257, published Mar. 26, 1990, each incorporated herein by reference) having the ability to specifically target, cleave and inactivate HIV RNA.

The sequence requirement for the hairpin ribozyme is any RNA sequence consisting of NNNG/CN*GUCNNNNNNNN (SEQ ID No. 15) (where N*G is the cleavage site, and where N is any of G, U, C, or A). The sequence requirement at the cleavage site for the hammerhead ribozyme is any RNA sequence consisting of NUX (where N is any of G, U, C, or A and X represents C, U or A) can be targeted. Accordingly, the same target within the hairpin leader sequence, GUC, is useful for the hammerhead ribozyme. The additional nucleotides of the hammerhead ribozyme or hairpin ribozyme is determined by the target flanking nucleotides and the hammerhead consensus sequence.

Cech et al. (U.S. Pat. No. 4,987,071, issued Jan. 22, 1991) has disclosed the preparation and use of certain synthetic ribozymes which have endoribonuclease activity. These ribozymes are based on the properties of the Tetrahymena ribosomal RNA self-splicing reaction and require an eight base pair target site. A temperature optimum of 50° C. is reported for the endoribonuclease activity. The fragments that arise from cleavage contain 5' phosphate and 3' hydroxyl groups and a free guanosine nucleotide added to the 5' end of the cleaved RNA. In contrast, the ribozymes of this invention hybridize efficiently to target sequences at physiological temperatures, making them suitable for use in vivo, not merely as research tools (see, column 15, lines 18–42, of Cech et al., U.S. Pat. No. 4,987,071).

The ribozymes of this invention and DNA encoding the ribozymes, described in more detail below, can be chemically synthesized using methods well known in the art. (For example, according to recommended protocols of Promega, Madison, Wis., USA, incorporated herein by reference). The ribozymes also can be prepared from a DNA molecule (that upon transcription, yields an RNA molecule) operably linked to an RNA polymerase promoter, e.g., the promoter for T7 RNA polymerase or SP6 RNA polymerase. Accordingly, also provided by this invention is a nucleic acid molecule, i.e., DNA or cDNA, coding for the ribozymes of this invention. When the vector also contains an RNA polymerase promoter operably linked to the DNA molecule, the ribozyme can be produced in vitro upon incubation with RNA polymerase and nucleotides. In a separate embodiment, the DNA is inserted into an expression cassette or transcription cassette as described in Cotten and Birnstiel (1989) *EMBO J.* 8(12):3861–3866 and in Hempel et al., *Biochemistry* 28:4929–4933 (1989), or Yu et al., *P.N.A.S.* 90:6340–6344 (1993), each incorporated herein by reference. A more detailed discussion of molecular biology methodology is disclosed in Sambrook et al. (1989) *Molecular Cloning: A Laboratory Manual*, Cold Spring Harbor Press, incorporated herein by reference. After synthesis, the RNA molecule can be modified by ligation to a DNA molecule having the ability to stabilize the ribozyme and make it resistant to RNase. Alternatively, the ribozyme can be modified to the phosphothio analog for use in liposome delivery systems. This modification also renders the ribozyme resistant to endonuclease activity.

The DNA molecule also can be in a host prokaryotic or eukaryotic cell in culture or in the cells of an organism. Appropriate procaryotic and eucaryotic cells can be transfected with an appropriate transfer vector containing the DNA molecule encoding a ribozyme of this invention. When the DNA molecule is operatively linked to a promoter for RNA transcription, the RNA can be produced in the host cell when the host cell is grown under suitable conditions favoring transcription of the DNA molecule. The vector can be, but is not limited to a plasmid, a virus, a retrotransposon or a cosmid. Examples of such vectors are disclosed in U.S. Pat. No. 5,166,320, incorporated herein by reference. A suitable adenoviral vector such as adeno-associated vector type 1 ("AAV-1") or adeno-associated vector type 2 ("AAV-2") (see Chatterjee et al., (1992) *Science* Vol. 258:1485–1488, incorporated herein by reference) are particularly useful. Methods of gene therapy are well known in the art, see, for example, Larrick, J. W. and Burck, K. L. *Gene Therapy: Application of Molecular Biology*, Elsevier Science Publishing Co., Inc., New York, N.Y. (1991) and Kreigler, M. *Gene Transfer and Expression: A Laboratory Manual*, W. H. Freeman and Company, New York (1990), each incorporated herein by reference.

Also provided by this invention is a pol III transcription cassette which is present in vectors such as pMJV and pMJT. These cassettes have the sequences listed below:

pMJT

5'-AAG CTT TGT AAC CGT TGG TTT CCG TAG TGT AGT GGT TAT CAC GTT CGC CTC ACA CGC GAA CGG TCC CCG GTT CGA AAC CGG GCG GAA ACA GGA TCC . . . (insert of foreign gene) . . . ACG CGT TTT TGC ATT TTT CTG CAG GCA TGC AAG CTT-3' (SEQ. ID NO. 17); and pMJV 5'-ATC GAT AAG CTA ATT CGA GAG CCT GTA AGC GGG CAC TCT TCC GTG GTC TGG TGG ATA AAT TCG CAA GGG TAT CAT GGC GGA CGA CCG GGG TTC GAA CCC CGG ATC C . . . (insert of foreign gene) . . . ACG CGT TTT TGC ATT TTT CTG CAG GCA TGC AAG CTT-3' (SEQ. ID NO. 18).

Also provided herein is a vector comprising the pol III transcription cassette and a foreign gene. Host cells and methods of expression using these transcription cassettes also are provided herein. This transcription cassette is useful for expression of genes or DNA sequences and is not intended to be limited to expression of the HIV ribozymes disclosed herein.

To produce the ribozymes with a vector, the nucleotide sequences coding for ribozymes are placed under the control of a strong promoter, e.g., lac, SV40 late, SV40 early, or lambda promoters. Ribozymes are then produced directly from the transfer vector in vivo.

In a separate embodiment, the viral vector is a retrovirus, such as a non-virulent vaccinia based viral vector or a Moloney murine leukemia virus. An appropriate retroviral vector for such gene therapy is a self-replicating retrovirus having inserted between the 5' and 3' long terminal repeat (LTR) regions of the retrovirus a foreign nucleic acid (DNA or cDNA) sequence, under the control of a promoter, for example, the retroviral LTR or an inserted pol III promoter such as the human tRNA$^{Val}$ promoter or the adenovirus VA1 promoter. The retroviral vector than stably expresses the ribozyme in the host cell.

One aspect of this invention provides a retroviral vector which can be used for in Vitro detection of the presence of HIV from a patient sample or to purify tissue samples of HIV prior to infusion into a patient. When used as an in vitro detection system, a sample of cells suspected of harboring the virus is removed from a mammal. "Mammal" is intended to include, but not be limited to primates, murine and human patients. The retroviral vectors are transduced into the cells and the cells are then propagated. Nucleic acid isolated from the cells is then probed (by hybridization analysis) for the presence of a fragment of HIV not present when the cell is not contacted with a ribozyme containing retroviral vector. Presence of a ribozyme specific fragment is a positive indication of the presence of HIV. This can be detected by the use of labels, such as radioisotopes or enzymes, in the assay. In vivo, the retroviral vectors can be used in gene therapy against HIV infection and replication. The retroviral vector of this invention is an infectious retroviral vector having inserted between the 5' and 3' long terminal repeat (LTR) regions of the retrovirus a foreign nucleic acid (DNA, RNA or cDNA) sequence, under the control of a pol III promoter. The retroviral vector then stably expresses the foreign gene product in host cell. As used herein, the term "infectious" means that the retrovirus vector has the ability to infect, integrate and express the foreign nucleotide sequence. For the purpose of illustration only, suitable retrovirus useful for the construction of retroviral vectors of this invention include the Moloney murine leukemia virus, the HIV-1 and the HIV-2 derived retroviral vectors. A foreign nucleic acid sequences includes, but is not limited to, a nucleic acid sequence encoding an anti-HIV-type specific agent such as an anti-HIV anti-sense molecule or a ribozyme that specifically cleaves HIV or an HIV regulatory sequence such as TAR.

In one embodiment, the nucleic acid sequence encodes a ribozyme specific for an HIV-type 1 or an HIV-type 2 virus. In one specific embodiment, a retroviral vector is shown expressing a ribozyme that specifically cleaves various strains of the HIV-type 1. One HIV-1 type specific ribozyme specifically cleaves a conserved sequence in the HIV-1 virus, found within the leader sequence of various strains of HIV-1, but not HIV-2.

A ribozyme target found at the 3' end of the HIV genome is the sequence:

5'-A C U G G G U C U C U C U G G U U A G-3'.

(SEQ. ID No. 5, designated an Rz-2 target sequence)

This sequence is approximately nucleotides 9079 through 9097 from the mRNA start U3/R boundary. Another example is the Rev/ENV region of the HIV genome. This sequence is 5' TTGGAGTCAGGAACTA 3' (SEQ ID No.

16). This sequence is 8629 through 8644 of HBX2. Also included within the scope of this invention are sequences which are substanitally similar to these sequences. "Substantially similar" or "substantially the same" includes those ribozyme sequences having the ability to target and block HIV infectivity as do the sequences shown above. Substantially similar sequences are those which can hybridize to the sequence or its complement under stringent conditions. Methods of hybridization are well known to those of skill in the art, see Sambrook, et al. infra, incorporated herein by reference.

Alternatively, ribozymes which specifically cleave conserved sequences in various strains of HIV-2 can also be constructed and expressed in vivo using the teachings set forth below.

Further provided by this invention are retroviral vectors having inserted between the 5' and 3' LTR more than one foreign gene sequence, each foreign gene sequence under the control of a separate pol III promoter or alternatively, under the control of single pol III promoter. The foreign gene sequences can encode the same or different gene products, for example, a nucleic acid encoding an anti-HIV-1 antisense molecule can be inserted within the same retroviral vector as a nucleic acid sequence encoding an HIV-1 specific ribozyme. Such retroviral vectors have the advantage of providing multi-functional therapy against HIV infection, each specific therapy working in synergy. In addition, because only a limited number of vectors are used, the number of integration sites in the host cell are reduced thereby reducing the possibility of activation of host cellular DNA sequences by the inserted retroviral vector.

Host cells stably transduced with the retroviral vectors described above also are provided by this invention. Suitable host cells include mammalian cells such as human or primate fibroblasts, peripheral blood lymphocytes, peripheral blood mononuclear cells, CD4$^+$T cells or hematopoietic stem cells. Also included within the scope of this invention is a mature, differentiated stem cell or a fetal umbilical cord blood cell having inserted therein prior to maturation, a retroviral vector described above. This differentiated stem cell now constitutively and stably express the foreign gene product. Methods of transducing retroviral vectors are well known to those of skill in the art. See, for example, Larrick, J. W. and Burck, K. L. *Gene Therapy: Application of Molecular Biology*, Elsevier Science Publishing Co., Inc. New York, N.Y. (1991), incorporated herein by reference.

A method of interfering with or preventing HIV viral replication in a cell infected with HIV is provided by this invention. This method requires transducing the cell with a retroviral vector having inserted between the 5' and 3' LTR of the retrovirus a nucleic acid sequence encoding an anti-HIV-type specific agent such as a ribozyme described above, under the control of an inserted pol III promoter. The target cell is transduced under conditions favoring insertion of the vector into the target cell and stable expression of the nucleic acid encoding the HIV-type specific ribozyme. The target cell can include but is not limited to mammalian cells. Suitable mammalian cells include, but are not limited to primate or human cells such as fibroblasts, CD4$^+$ T cells, peripheral blood lymphocytes, fetal umbilical cord blood cell, peripheral blood mononuclear cells or hematopoietic stem cells. If the cell is transduced prior to HIV infection, infection of the target cell or its progeny can be prevented.

Fetal cord blood can be collected from normal new born, new born of HIV infected individual, or from the mother during the process of delivery. The blood can be frozen using programmed freezing to ensure maximal viability.

As used herein, the term "interfering with or preventing" HIV viral replication in a cell means to reduce HIV replication or production of HIV components necessary for progeny virus in a cell as compared to a cell not being transiently or stably transduced with the retroviral vector. Further encompassed within this term is a decrease in the relative production of infectious virions, which may occur by cleavage of the packaged progeny RNA. A simple and convenient assay to determine if HIV viral replication has been reduced is the ELISA assay for the HIV p24 antigen (gag gene product). Alternatively, total RNA from transduced and infected "control" cells can be isolated and subjected to analysis by dot blot and probed with HIV specific DNA to determine if HIV replication was reduced. A greater than fifty percent reduction in HIV replication as compared to control cells quantitates a prevention of HIV replication.

For the purposes of this invention, HIV is intended to encompass any variant HIV, e.g., HIV-1, HIV-2 or unclassified clinical isolates. An unexpected advantage of this invention is its efficacy against various strains of any type or variant of HIV.

In one embodiment of this invention, the target cell can be removed from a mammal, e.g., a primate or human patient, using methods well known to those of skill in the art and transduced as noted above. The transduced target cells are then be reintroduced into the same animal or a different animal of the same species.

The following examples are intended to illustrate but not limit the invention.

EXPERIMENTAL DETAILS

Experiment No. 1

Enzymes and Chemicals. All restriction enzymes used were from either Bethesda Research Laboratories (BRL) or Boehringer Mannheim Biochemicals. The buffers for restriction enzymes were supplied by the manufacturers. T4 DNA ligase and the sequencing kit were obtained from Pharmacia. The in vitro transcription kit and relevant enzymes were obtained from Promega. Bovine calf serum, antibiotics (penicillin and streptomycin), L-glutamine, sodium pyruvate, phosphate-buffered saline (PBS) and Dulbecco modified Eagle medium (DMEM) were purchased from GIBCO. The HIV-1 p24 antigen detection kit was obtained from Coulter and used according to the manufacturer's instructions.

Figure 1:
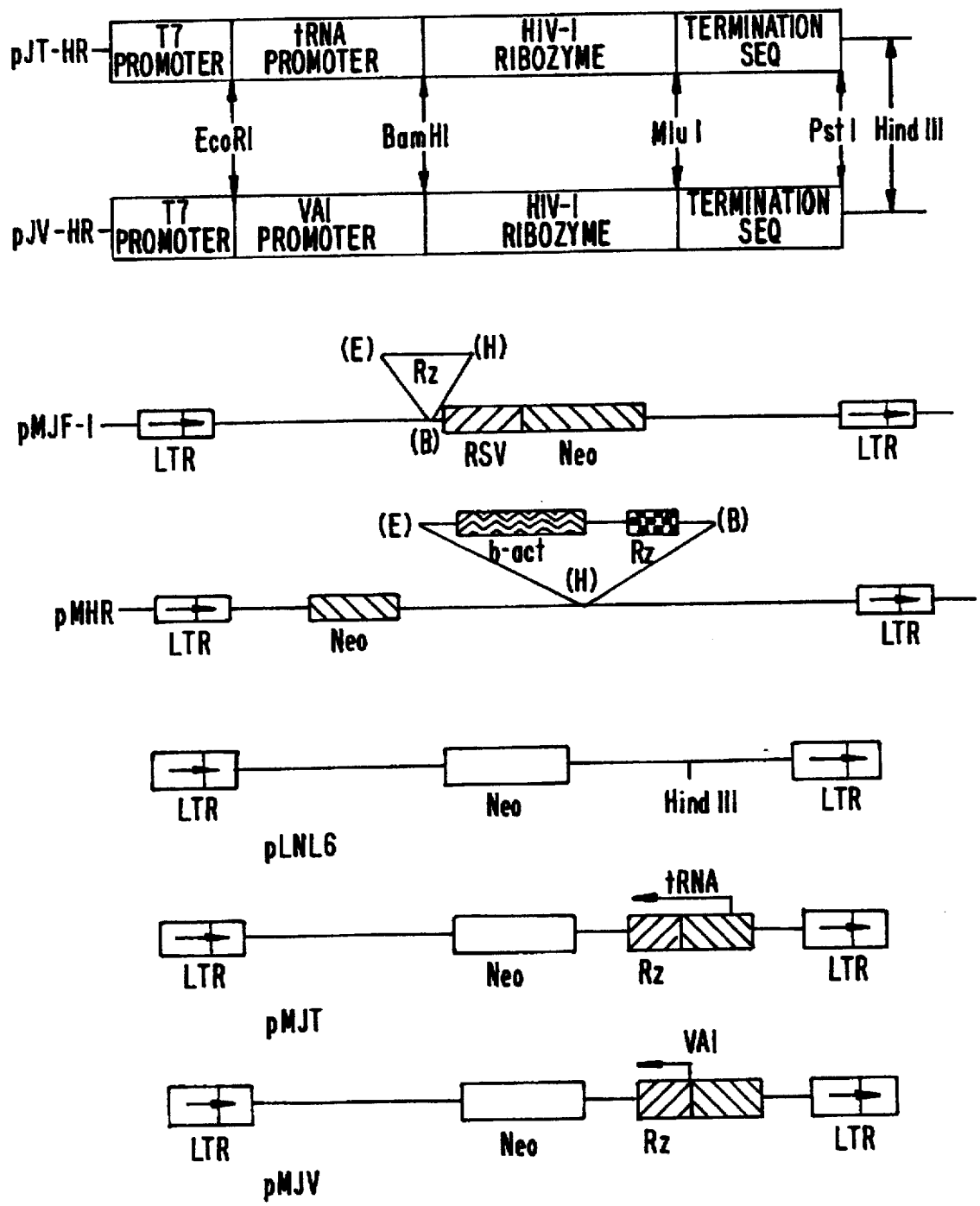
FIG. 1. Schematic representation of the various plasmid and retroviral vectors containing HIV-specific ribozyme gene designated "Rz-1" (not drawn to scale). See the Detailed Description of the Invention for the designing of each plasmid.

Construction of pol III driven ribozyme plasmids. Unless stated otherwise, all recombinant DNA techniques were performed as described in Sambrook et al., *Molecular Cloning: A Laboratory Manual*, Cold Spring Harbor Lab., Cold Spring Harbor, N.Y. (1989), incorporated herein by reference. The HIV-1 5' leader sequence-specific hairpin ribozyme (5'-ACA, CAA, CAA, GAA, GGC, AAC, CAG, AGA, AAC, ACA, CGT, TGT, GGT, ATA, TTA, CCT, GGT, A-3' (SEQ. I.D. No. 13)) was cloned as follows: chemically synthesized double-stranded deoxyribonucleotides corresponding to human tRNA$^{val}$ promoter (138 bp) and adenovirus VA1 (104 bp) promoter were cloned into pHR and pdHR (Ojwang et al., *Proc. Natl. Acad. Sci. USA* 89:10802–10806 (1992), incorporated herein by reference) plasmids (which contain the active and disabled ribozymes respectively) upstream of the ribozyme coding sequence at EcoRI-to-BamHI sites (FIG. 1). The resultant plasmids containing the pol III promoters were digested with Mlu I and Pst I to remove the autocatalytic cassette and replace it with pol III termination sequences as outlined in Geiduschek, E. P., *Ann. Rev. Biochem.* 57:873–914 (1988) incorporated herein by reference. The sequences of the clones were confirmed by DNA sequencing. The plasmid vectors were designated pJT-HR for the plasmid containing the tRNA$^{Val}$ promoter and pJV-HR for the plasmid containing the VA1 promoter constructs (FIG. 1).

The HIV-1 specific ribozyme cleaves between two bases found at positions 111/112 as counted from the 5' cap site.

Construction of Retroviral Vectors. The vectors in which the ribozyme was driven by the internal pol III promoters were constructed as follows: the fragment containing the human tRNA$^{val}$ or adenovirus VA1 pol III promoter-ribozyme (Rz) cassette (including the pol III termination signal) was removed from pJT-HR or pJV-HR (the plasmid in which a synthetic tRNA or VA1 promoter was constructed to drive the HIV leader sequence hairpin ribozyme, (Yu et al., *P.N.A.S.* (1993), incorporated herein by reference) by digestion with Hind III, and inserted to the Hind III site of the retroviral vector pLNL6 (from Dr. Fred Levine of University of California, San Diego). The internal promoter transcription cassette is now in the opposite orientation with regard to the LTR of the vector. The resulting retroviral vectors were designated pMJT (for tRNA$^{VA1}$ internal promoter) and pMJV (for VA1 internal promoter, FIG. 1).

A retroviral vector with an internal β-actin promoter was constructed using the same vector, with an EcoRI-BamHI insert taken from pβ-HR (Ojwang et al. supra). The hairpin autocatalytic cassette (Ojwang et al. supra) is included in the latter insert. The resulting retroviral vector after ligation was named pMHR (FIG. 1). In order to compare the ribozyme expression from the internal promoters versus the retroviral LTR, another vector (pLRNL-2, from Dr. Jiing-Kuan Yee of University of California, San Diego) was used. A ribozyme sequence was excised from pHR by EcoRI and Hind III digestion and was inserted into the Hind III cloning site, after both the insert and the linearized vector were blunt-ended. The ribozyme sequence was placed immediately upstream of RSV promoter which drives neo gene (FIG. 1).

Samples of the retroviral vectors pMJV and pMJT were deposited with the American Type Culture Collection (ATCC) 12301 Parklawn Drive, Rockville, Md. 20852. These samples were deposited on May 17, 1993 under the provisions of the Budapest Treaty on the International Recognition of the Deposit of Microorganisms for the Purpose of Patent Procedure and were accorded ATCC Accession Nos. 75471 and 75470, respectively.

Multi-target ribozyme-expression vectors. To ensure the efficacy of the ribozyme gene therapy for HIV infection, multi-target ribozyme expression vectors (FIG. 15) were constructed. A dicistronic retroviral vector, pLPONL (Jiing-Kuan Yee, University of California at San Diego) was utilized. The anti-leader ribozyme gene (Rz-1) including tRNA$^{val}$ or VA1 promoters is removed from pMJT or MJV (FIG. 1). A ribozyme gene (Rz-2), which targets a segment of the HIV-1 3' sequence, was cloned in front of the internal translation initiation site (PO) from the untranslated region of poliovirus. Results of transient co-transfection showed the inhibitory effects of these constructs on HIV-1 expression as demonstrated by reduced p24 production. Jurkat cell lines can stably express both of these ribozymes. Other ribozymes and/or antisense sequences can also be incorporated in these constructs.

Cells and Transfections. HeLa cells were propagated in DMEM containing 10% fetal bovine serum (FBS), 100 µg/ml penicillin-streptomycin, 2 mM L-glutamine and 1 mM sodium pyruvate. Cells were grown to about 70% confluence in a 12-well plate ($1\times10^5$ cells/well) which were plated out one day prior to transfection. Before transfection, the medium was replaced with 2 ml of fresh DMEM containing the same additives. Calcium-phosphate-precipitated plasmid DNA was added to the cells. After 12 to 24 hours the medium was removed and the cells were washed two or three times with 1× PBS. The cultures were then maintained in 2 ml of DMEM containing 10% FBS, 100 µg/ml penicillin-streptomycin, 2 mM L-glutamine and 1 mM sodium pyruvate.

Stable cell lines. To generate retroviral particles, the amphotropic packaging cell line PA317 was transfected by the calcium-phosphate method, Sambrook et al., (1989) supra., as follows: subconfluent PA317 cultures were transfected with 20 µg each of calcium-phosphate precipitated pLNL6, pMJF-1 or pMJT for 12 hours in Dulbecco's modified Eagle's medium (GIBCO) supplemented with 1 mM sodium pyruvate, 100 units/ml penicillin, 100 µg/ml streptomycin, 13 µg/ml hypoxanthine, 3.9 µg/ml thymidine, 18 ng/ml aminopterin and 10% fetal bovine serum (FBS; Gemini Bioproducts) in 100-mm tissue culture dishes. The cells were washed twice with phosphate-buffered saline (pH 7.4, $Ca^{2+}$- and $Mg^{2+}$-free) and then incubated for an additional 24 hours in fresh medium. The culture supernatants were used to infect human CD4$^+$ lymphocyte-derived Jurkat or Molt-4 clone 8 cells (Molt-4/8) (Kikukawa, R., et al., *J. Virol.* 57:1159–1162 (1986)). Jurkat and Molt-4/8 cells ($1\times10^6$ cells) were suspended in 5 ml each of the supernatants. After 4 hours, the supernatants were removed and the cells were cultured in RPMI-1640 medium (GIBCO) supplemented with 100 units/ml penicillin, 100 µg/ml streptomycin, 10% FBS and 400 µg/ml G418 (GIBCO). Resistant cells were selected by growth in G418-containing medium for up to 3 to 4 weeks. The G418-resistant Jurkat or Molt-4/8 cells transduced by pLNL6, pMJF-1 and pMJT were designated as JLNL6, JMJF-1 and JMJT or MLNL6, MMJF-1 and MMJT, respectively.

Expression of the ribozyme in stable cell lines. Total RNA from the stable cell line was extracted by the acid guanidinum thiocyanate-phenol/chloroform extraction method as described in Chomczynski and Sacchi, *Anal. Biochem.* 162:156–159 (1987), incorporated herein by reference. One µg of the total RNA after treatment with deoxyribonuclease I (RQ1 DNase; Promega) was used as the template for reverse transcription (RT). Polymerase chain reaction (PCR), combined with RT, was carried out (94° C. for 1 min, 45° C. for 1 min, 72° C. for 1 min; 30 cycles) with a primer pair of Rib 4 (5'-CAC, ACA, ACA, AGA, AGG-3' (SEQ. I.D. No. 1) and Rib 2 (5'-TAC, CAG, GTA, ATA, TAC, CAC-3' (SEQ. I.D. No. 2)) according to the method described previously, except that the extraction step with glass powder was omitted. See Yamada, O., et al., *J. Virol. Methods* 27:203–210 (1990), incorporated herein by reference. After the PCR with and without RT, 10 µl of each amplified product was subjected to electrophoresis on a 3% low melting agarose gel (Boehringer) in Tris-borate buffer (pH 7.2) and Southern blot analysis was performed with $^{32}$P-end-labeled Rib 3 (5'-CAA, CCA, GAG, AAA, CAC ACG, TT-3' (SEQ. I.D. No. 3) as previously described. See Yamada, O., et al. (1990) supra., incorporated herein by reference.

Proliferation of the stable cell lines. Cell-proliferation was determined by the level of [$^3$H]thymidine incorporated in the cells. Briefly, parental Jurkat cells and test cell lines were split into quadruplicate wells of a U-bottomed 96-well plate at $10^4$ cells/100 µl/well. One hundred µl RPMI-1640 supplemented with 10% FBS containing 1 µCi[$^3$H-methyl]

thymidine (NET-027; NEN) was added to each well. After 48 hours, the cells were harvested on filter paper. The radioactivity of the filter was measured in a scintillation spectrometer (Beckman).

HIV infection. HIV-1 strains HXB2, MN and Eli were produced from cloned HIV-1 pHXB2, (described in Starcich, B., et al., *Science* 227:538–540 (1985)), pMN (Gurgo, C., et al., *Vir.* 164:531–540 (1988)) and pEli (Alizon, M., *Cell* 46:63–74 (1986)), each incorporated herein by reference, respectively. Uncloned HIV-1 J677-2 was initially isolated by co-cultivation of peripheral blood mononuclear cells (PBMC) from an AIDS patient with normal PBMC, and subsequently passaged once through MT-4, a human CD4+ T-cell line hosting human T-cell leukemia virus type-I (HTLV-I). The infectious titer (TCID$_{50}$) of virus preparations of these virus strains was determined using MT-2, an HTLV-1 infected human CD4+ T-cell line, by the method described in Yamada, O., et al., *AIDS Res. Hum. Retroviruses* 4:287–294 (1988), incorporated herein by reference. In short-term culture experiments, these virus strains were used to infect Jurkat cells expressing the ribozyme (JMJF-1 and JMJT) and control Jurkat cells (JLNL6) at the input m.o.i. of 0.01 or 0.1 for the slower growing strain J677-2. In long-term culture experiments, HXB2 and MN were used to infect JMJF-1, JMJT and JLNL6 at the input m.o.i. of 0.01. The HIV-2 KR strain was produced from an infectious molecular clone described in Talbott, R., et al., *P.N.A.S., USA* 90:4226–4230 (1993), incorporated herein by reference. The TCID$_{50}$ of the HIV-2 KR preparation was determined for the infection of Molt-4/8 cells by the method of Yamada, O., et al., (1988), supra. In short-term culture experiments, HXB2 and HIV-2 KR were used to infect Molt-4/8 cells expressing the ribozyme (MMJF-1 and MMJT) and Molt-4/8 cells transduced by the control retroviral vector (MLNL6) at the input m.o.i. of 0.01 and 0.001, respectively. The cells were washed twice with RPMI-1640 medium after virus adsorption for 2 hours, and resuspended in RPMI-1640 supplemented with 10% FBS at the concentration of $10^5$ cells/ml. In short-term culture experiments, the infected cells were cultured for 6 days, small aliquots of the culture fluid were collected every second day, and the level of HIV-1 p24 antigen or HIV-2 p26 antigen was determined by HIV-1 or SIV/HIV-2 antigen capture ELISA test (Coulter). In long-term culture experiments, at day 5 and thereafter, the infected cells were divided every second day to maintain $3\times10^5$ cells/ml. The culture supernatants were tested for the presence of HIV reverse transcriptase (RT) activity. Briefly, 0.24 ml 30% polyethylene glycol 6000 and 20 µl 4M NaCl were added to 0.5 ml of the supernatants in duplicate. After microcentrifugation at 14000×g for 30 min, the supernatants were removed and 10 µl each of TNE solutions (0.1% Triton×100, 10 mM Tris-HCL pH 7.8, 100 mM NaCl, 1 mM EDTA) was added to the tubes. After mixing, 40 µl of a mixture containing 62.5 mM Tris-HCL pH 7.8, 25 mM MgCl$_2$, 25 mM KCl, 2.5 mM dithiothreitol, 31.25 µg/ml poly(rA)p(dT)$_{12-18}$ (Pharmacia), 62.5 µCi/6.25 nmol/ml of [$^3$H]dTTP (NEN) was added and incubated at 37° C. for 1 hour. Ten µl 0.2M EDTA was added. A sample (50 µl) of the mixture was then spotted on DE81 paper (Whatman), air-dried, washed three times with 5% sodium pyrophosphate and twice more with water. The paper was then dried and the radioactivity was measured by a scintillation spectrometer (Beckman).

Rechallenge of recovered virus after long-term culture. The culture supernatant of JMJF-1 cells infected with HIV-1 HXB2 or MN strains collected on day 35 or day 23, respectively, in the experiment shown in FIG. 12 was used to reinfect the JLNL6, JMJF-1 and JMJT cells. The input m.o.i. was 0.0004 and 0.01 in HXB2 and MN, respectively (because the infectivity of HXB2 collected on day 35 was very low, input m.o.i. could not be adjusted to 0.01). These infected cells were cultured for 6 days. Small aliquots of the culture fluid were collected every second day and the level of p24 antigen was determined by HIV-1 antigen capture ELISA test (Coulter).

Semi-quantitative double PCR of viral DNA. Cellular genomic DNA was extracted from JLNL6 and JMJT cells 6 hours after infection with HIV-1 HXB2 by the method using proteinase K and phenol/chloroform as described in Sambrook et al., supra. One µg each of the DNA extracts was used as template for the first PCR. The composition of the reaction mixture for the first and second PCR was 50 mM Tris pH 8.3, 6 mM MgCl$_2$, 40 mM KCl, 1 mM dithiothreitol, 200 mM each of dATP, dGTP, dTTP and dCTP, 1 mM each of the primers and 2.5 units Taq polymerase (Promega). Primer pairs for HIV-1 LTR were used for the amplification of HIV-1 DNA (the amplified product includes the target sequence to the ribozyme). The first PCR was carried out (94° C. for 1 min, 54° C. for 1 min, 72° C. for 1 min: 30 cycles) with the primer pair SK29, see Talbott, R., et al., *P.N.A.S.* (1993) supra., and GK2 (5'-CGG, CGG, ATC, CCG, GGC, GCT, TCA, GCA, AGC, CGA-3' (SEQ. I.D. No. 14)). A primer pair for β-globin which is PC03/GH21, see Saiki, R., et al., *Science* 239:487–491 (1988), incorporated herein by reference, was added to the same reaction tubes after the tenth cycle of the first PCR as an internal control. For the second PCR, one-tenth volume of the first PCR product was added and amplification was carried out (30 cycles) with both primer pairs SK29/SK30, (see Talbott, R., et al., (1993), supra.), and RS06/GH21, (see Saiki, R., et al., (1988), supra.). Ten µl each of the second PCR products was collected every fifth cycle and the amplified products were detected by gel electrophoresis and Southern blot analysis. Southern blot analysis was performed separately by hybridization with $^{32}$P-end-labeled SK31 (Talbott, R., et al., (1993), supra.) or RS06 for HIV-1 or β-globin, respectively. To estimate the relative amounts of HIV-1 DNA in the cellular DNA extracts, different concentrations (0.05–500 fg/ml) of HIV-1 SF2-containing plasmid DNA (see Sanchez-Peseador, R., et al., *Science* 227:484–492 (1985), incorporated herein by reference) were amplified using the same primers and conditions.

p24 Antigen Quantification. The Coulter HIV-1 p24 ELISA kit was used to quantitate the core antigen according to the manufacturer's instructions. Optical density was measured at 450 nm using an ELISA plate reader. Viral protein (p24) concentration in the culture supernatant harvested 40 to 48 hours after transfection was determined from the absorbance using a standard curve. The values were then expressed as percentage of activity or directly by the p24 protein concentration. The amount percentage inhibition of expression of HIV-1 p24 was used to determine the effectiveness of the ribozyme as an inhibitor of HIV-1 replication and expression. HIV-2 p26 was quantified using similar methodology (Coulter).

Dot-blot Analysis. Total RNA from HeLa cells transfected with different DNA samples was isolated using the procedure previously described in Ojwang et al., supra, incorporated herein by reference. Briefly, the cells were washed twice with ice-cold 1× PBS and then lysed by adding 10 mM EDTA (pH 8.0), 0.5% SDS, 0.1M sodium acetate (pH 5.2). Total RNA was recovered from the cell lysates by a single extraction with water-saturated phenol and ethanol precipitation. To remove the template DNA, the isolated RNA was subjected to DNase I treatment. The reaction was stopped by adding 10 mM EDTA and 0.2% SDS and the RNA was extracted by phenol:chloroform treatment and finally by ethanol precipitation. The recovered total RNA was redissolved in DEPC-treated water, and 20 μg were immobilized on GeneScreen Plus membrane (Dupont) by gentle suction with a blotting manifold (Bethesda Research Laboratory). The membrane was then probed with a 5'-end radioactively labeled synthetic DNA probe complementary to the ribozyme RNA or in vitro transcribed and internally radiolabeled RNA probe complementary to HIV-1RRE RNA. The intensity of the dots was quantified by a phosphoroimager (Molecular Dynamics, California).

Effects of the Ribozyme Driven by pol III Promoters on HIV-1 Expression. Human tRNA$^{VA1}$ and VA1 promoters were inserted upstream of the HIV-1 5' leader sequence-specific ribozyme gene. The pol III termination site was inserted downstream of the ribozyme gene using the method disclosed in Ratner et al., *AIDS Res. Hum. Retroviruses* 3:57–69 (1987), incorporated herein by reference. The expression of the ribozyme in HeLa cells transfected with these plasmids was determined by RNA dot blot analysis. When compared with the previously described pol II promoter human β-actin (described in Chang et al., *Clinical Biotech.* 2:23–31 (1990), incorporated herein by reference) the expression of the ribozyme driven by pol III promoters was 88% higher.

Figure 2A:
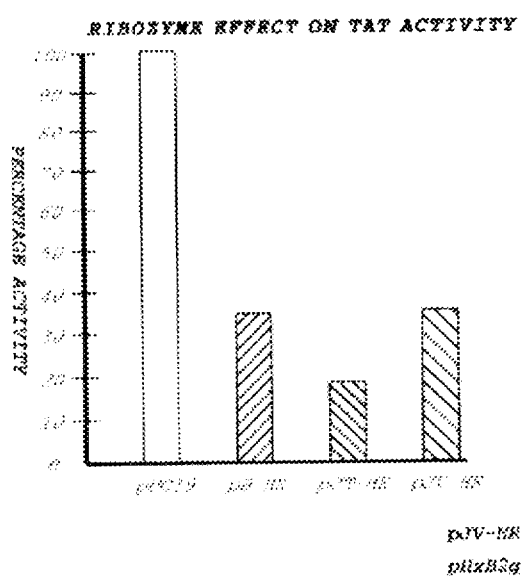
FIGS. 2A through 2C. Effect of anti-HIV-1 specific ribozyme on HIV-1 expression in a transient assay. The effector plasmid (pHXB2gpt as described in Ratner, L. et al. *AIDS Res. Hum. Retroviruses* Vol 3:57–69 (1987), incorporated herein by reference) and a reporter plasmid (pC15CAT) were triple transfected into HeLa cells either pUC19 or with the anti-HIV-1 ribozyme containing plasmid pβ-HR, pJT-HR or pJV-HR separately in a ratio of 1:10 µg (effector plasmid:ribozyme plasmid). Each bar is labeled by the name of their plasmid.
Figure 2B:
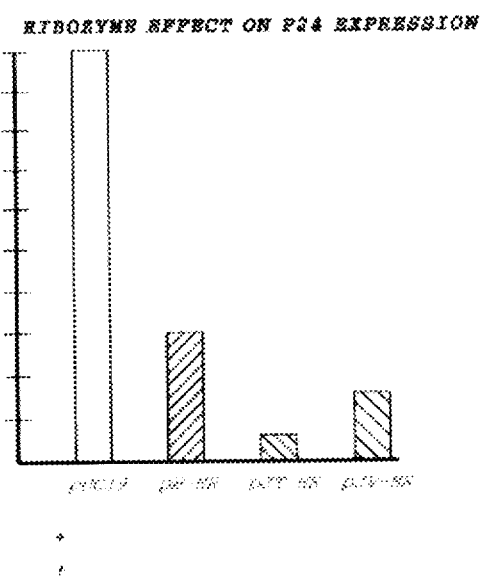

To determine the effectiveness of ribozyme-mediated inhibition of HIV expression in a transient assay, the effector plasmid (pHXB2gpt) and a reporter plasmid (pC15CAT) (Arya et al., *Science* 229:69–73 (1985) incorporated herein by reference) were co-transfected into HeLa cells with the ribozyme containing plasmids (pJT-HR and pJV-HR) or pUC19 as the control by calcium phosphate method as described in Ojwang et al., supra. For comparison, the same ribozyme driven by β-actin promoter reported in Ojwang et al., supra, was used in parallel. Cell lysates were subjected to CAT assay, and the levels of HIV-1 p24 antigen (gag gene product) in the culture supernatant were analyzed by enzyme-linked immuno-absorbent assay (ELISA). The results obtained were graphed as relative percentage of control value as 100% (FIGS. 2A and B). The HIV-1 ribozyme expressed by pol III promoters inhibited HIV-1 expression and virus production significantly (overall 70–95%). In the assay for Tat protein activity (FIG. 2A), the ribozyme directed by tRNA$^{va1}$ promoter yielded more than 10% greater inhibition than the ribozyme directed by β-actin promoter. For p24 expression (FIG. 2B), both pol III promoter-directed ribozymes yielded 15–25% more inhibition than the β-actin promoter directed ribozyme. Additionally, the effect of the ribozyme containing pol III promoter plasmids for the inhibition of HIV-1 expression was DNA dose-dependent.

Cleavage and Target Specificity of the Ribozyme. The β-actin promoter driven ribozyme inhibits HIV due to its catalytic and by not its antisense properties. In addition, its action is dependent on the presence of a target sequence. Similar function and specificity for the pol III-promoter driven ribozymes has now been found. To determine the contribution of catalytic versus antisense activity to the inhibition of HIV-1 expression, a disabled ribozyme (Ojwang et al., supra) having three point mutations (from 22-AAA-24 to 22-UGC-24) was constructed in pol III promoter plasmids. The point mutations rendered the ribozyme inactive, but had no effect on its binding to target RNA. Wild-type and disabled ribozymes were expressed at the same levels in transfected cells but the disabled ribozyme yielded only ~10% inhibition of HIV-1 expression. Therefore, the inhibition of HIV-1 replication and expression observed is mainly attributed to the catalytic property of the ribozyme and not to its antisense features. When pTAT was used to replace pHXB2$_{gpt}$ to supply Tat protein in trans, neither pJT-HR nor pJV-HR showed inhibition of CAT activity. This confirms that the HIV-1 ribozyme only inhibits expression of messengers containing the target sequence.

Figure 2C:
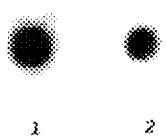

Equal amounts of total RNA from HeLa cells transfected with pHXB2gpt/pJV-HR (1:10 μg) and pHXB2gpt/pUC19 were subjected to dot blot and probed with HIV-1 specific DNA to determine if the reduced expression of HIV-1 proteins was a direct result of a reduced amount of HIV-1 mRNA. The result shown in FIG. 2C indicates that the presence of the ribozyme reduced the HIV-1 transcript by 71%. The level of viral protein p24 inhibition observed in vivo (80–90%, FIG. 2C) can be due to the fact that some viral mRNA is only partially degraded and is still detectable by dot blot but not translatable into proteins.

Figure 4A:
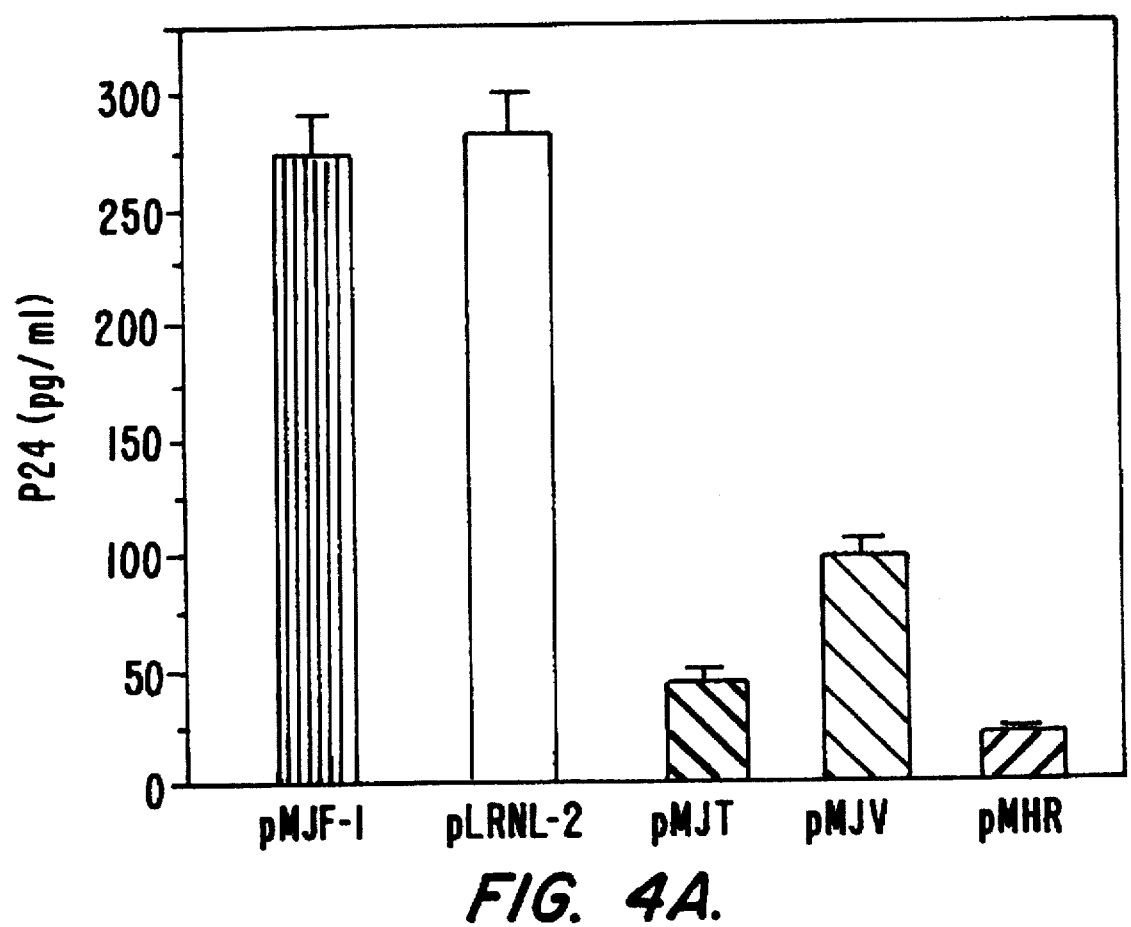
FIGS. 4A and 4B. Effect of anti-HIV-1 specific ribozyme on HIV-1 SF-2 expression and the ribozyme expression in retroviral vectors.
Figure 4B:
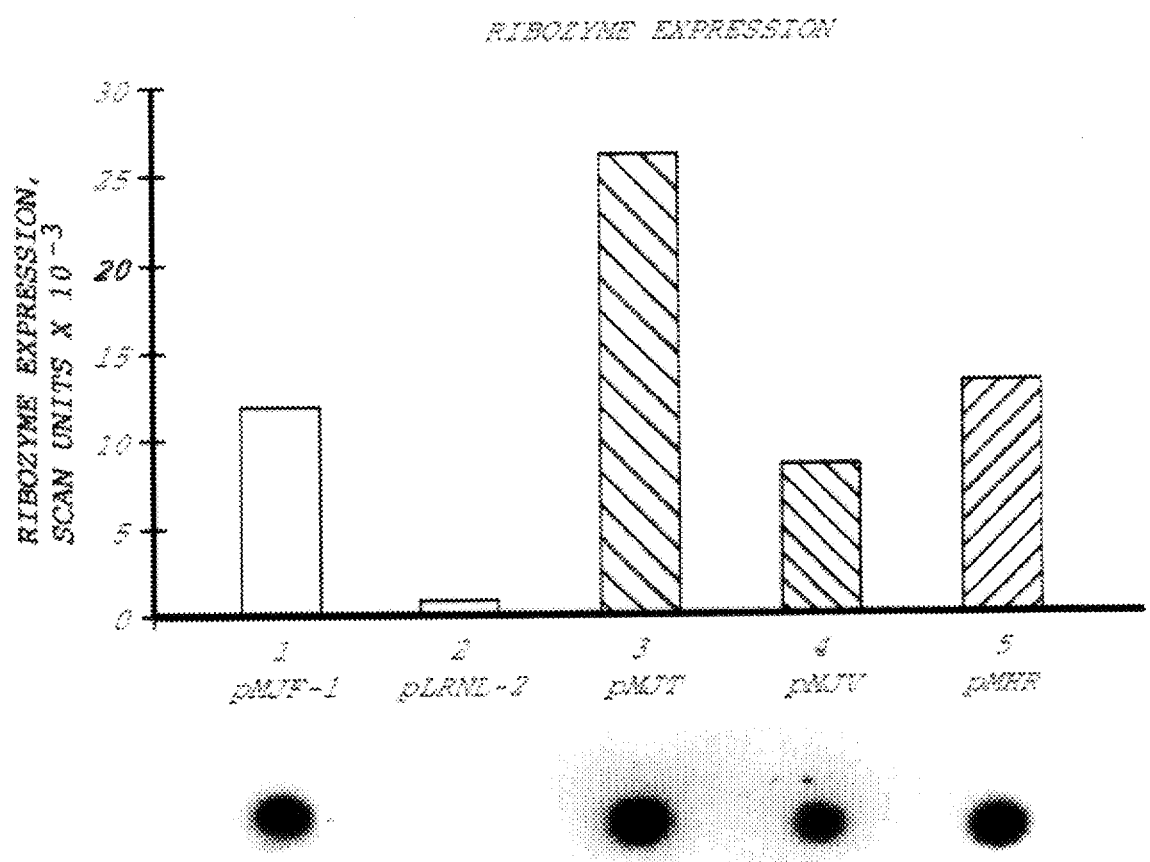

The Leader-sequence Ribozyme Inhibits Diverse HIV-1 Strains. A necessary feature of any effective therapeutic agent against HIV infection and AIDS is its ability to inhibit different HIV-1 strains. This important issue was addressed by using different retroviral vectors containing the ribozyme (FIG. 1) to co-transfect with DNA constructs from a variety of HIV-1 strains. Three strains, MN, SF-2, and Eli, were chosen, which exhibit varying genetic distance from HXB2, with Eli, a Zairian strain, being the most distant. Interestingly, the leader sequence targeted by the ribozyme under study is completely conserved among known HIV-1 strains, with the exception of that of MN, which has one base mutation (see Myers et al., *Human Retroviruses and AIDS* 1992, Theoretical Biology and Biophysics, N. Mex., incorporated herein by reference) (FIG. 3). As seen in FIG. 4A, all three retroviral vectors in which the ribozyme gene is driven by an internal promoters (FIG. 1) show significant inhibition of SF-2 expression (compare the three bars on the right to the control bar of the second from the left). These internal promoters include the previously reported pol II β-actin promoter (in pMHR) and the pol III promoters of tRNA$^{va1}$ and VA1 (in pMJT and pMJV) reported here. On the other hand, the retroviral vector pMJF-1 in which the ribozyme gene is driven directly by MoMLV LTR (FIG. 1) did not inhibit HIV-1 expression (FIG. 4A, compare the first two bars from the left). To determine whether the inability of pMJF-1 to inhibit SF-2 is due to the lack of expression of the ribozyme in this vector, RNA dot blot was carried out (FIG. 4B). Expression of ribozyme sequences was detected in all retroviral vectors carrying the ribozyme gene including pMJF-1. In contrast, the vector alone (bar #2) produced no ribozyme. In fact, pMJF-1 which did not inhibit the HIV-1 expression, is one of the high expression vectors. One explanation for the inability of this vector to inhibit virus expression is that the ribozyme cloning site is several hundred base pairs away from the transcription initiation point. The extra long arm attached at the 5' end of the ribozyme may interact with cellular nucleic acids or proteins, which affect its accessibility to the substrates.

Figure 5A:
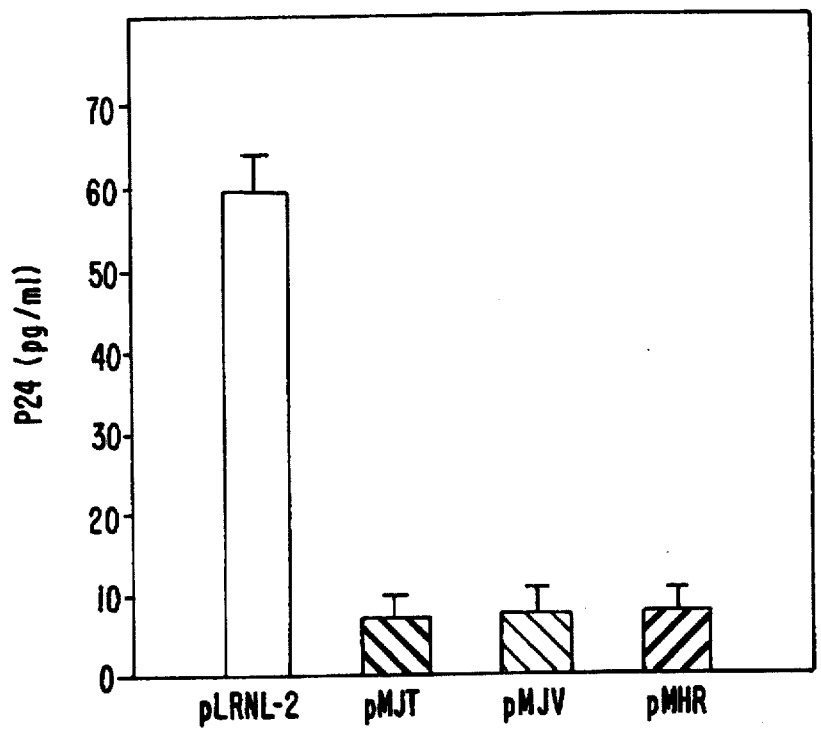
FIGS. 5A and 5B. Effect of anti-HIV-1 specific ribozyme expressed in retroviral vectors on HIV-1 Eli and MN strains expression in a transient assay. The effector plasmid (pEli or pMN) was co-transfected in duplicate or in triplicate into HeLa cells the ribozyme containing retroviral vectors pMJT, pMJV, and pMHR (bars 2, 3 and 4, respectively) or retroviral vector without ribozyme gene pLRNL-2 (bar 1).
Figure 5B:
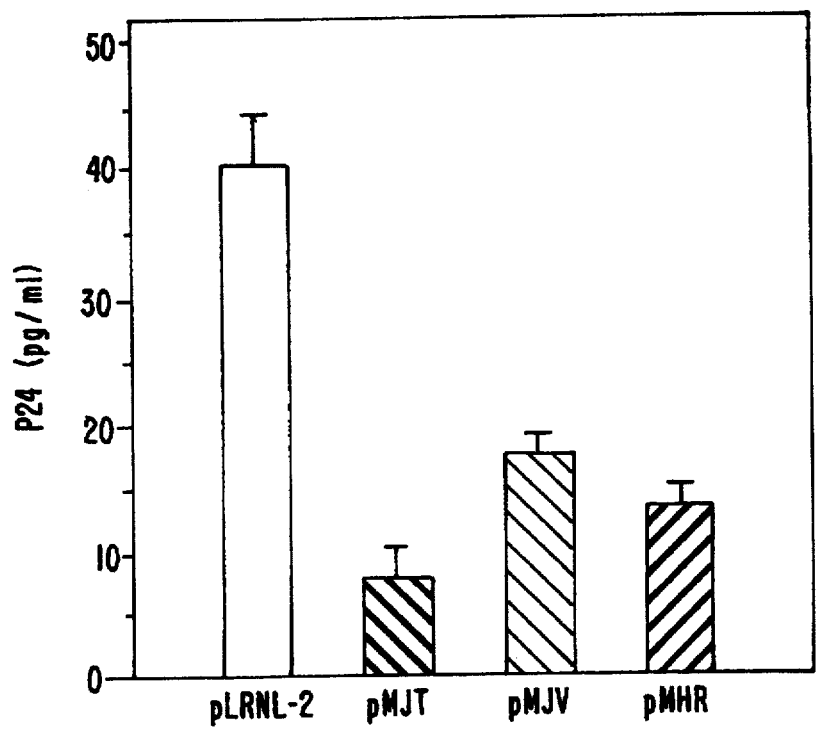

The effect of pMJT, pMJV and pMHR, on Eli and MN was then investigated. As shown in FIG. 5A, a similar extent of inhibition was observed for strains SF-2 and Eli (FIG. 4A and FIG. 5A). Slightly less but still significant inhibition was observed for the MN strain (FIG. 5B), suggesting that the single base substitution in target sequence has some effect on ribozyme activity, and more importantly, the hairpin ribozyme can tolerate certain mutations in the substrates.

Experiment No. 2

Derivation of T cell Lines Constitutively Expressing Ribozyme. The retroviral vectors pMJF-1 and pMJT (FIG. 1) were constructed from the parental vectors LNL-6 and LRNL-2 as described above. These plasmid DNAs as well as the pLNL6 vector control DNA were transfected into the amphotropic packaging cell line PA317, and the culture supernatants were used to infect the human CD4$^+$ T cell lines Jurkat and Molt-4/8. G418 resistant Jurkat or Molt-4/8 cells transduced by LNL6, MJF-1 and MJT were designated as JLNL6, JMJF-1 and JMJT or MLNL6, MMJF-1 and MMJT, respectively. Ribozyme expression in these cell lines was examined by the polymerase chain reaction combined with reverse transcription (RT-PCR), using primers contained within the ribozyme sequence (FIG. 6). An amplified product was detected only in JMJF-1, JMJT, MMJF-1 and MMJT and not in the vector alone controls (JLNL6 and MLNL6). Furthermore, the product was derived from RNA and not DNA since no amplification was observed in the absence of reverse transcription. Although the PCR assay was not designed to be quantitative, the expression levels of the ribozyme in JMJT and MMJT consistently appeared higher than those in JMJF-1 and MMJF-1, suggesting that the internal tRNA$^{val}$ promoter was more potent in driving expression. There was no deleterious effect of constitutive expression of the ribozyme on cell proliferation as evaluated by thymidine uptake (FIG. 7) or by cell number. Further, transduced and untransduced (parental) cells were indistinguishable with respect to viability ($\geq 99\%$) with passage at every 4 days for 3 months.

Figure 9A:
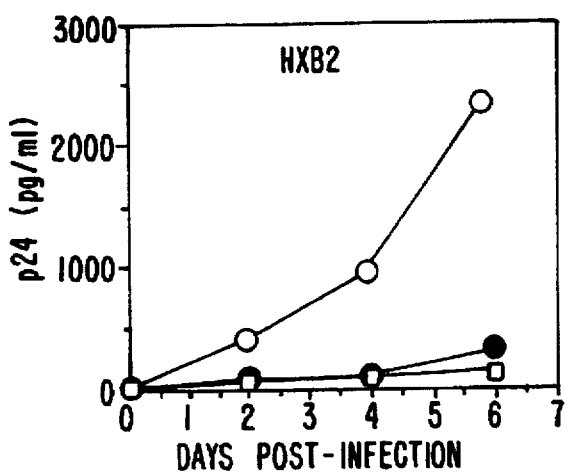
Figure 9B:
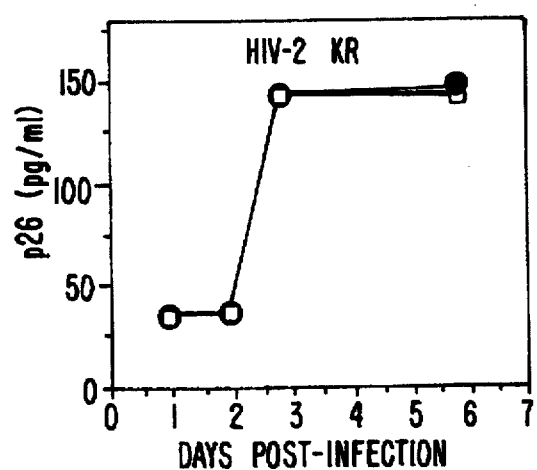
Figure 8A:
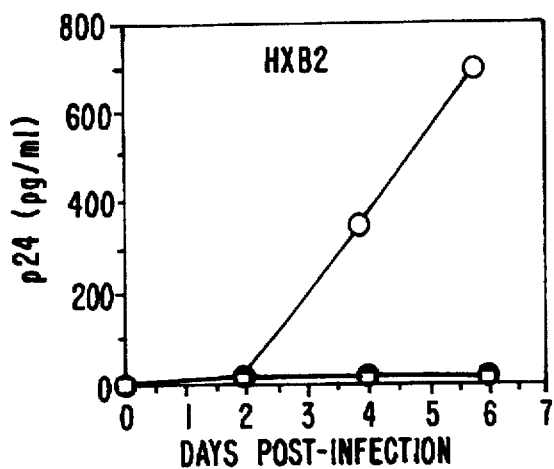
Figure 8B:
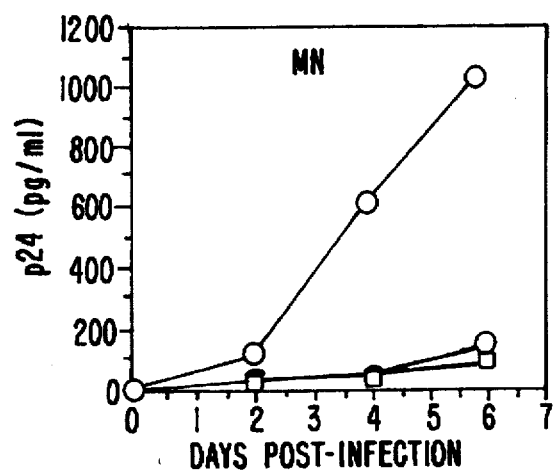
Figure 8C:
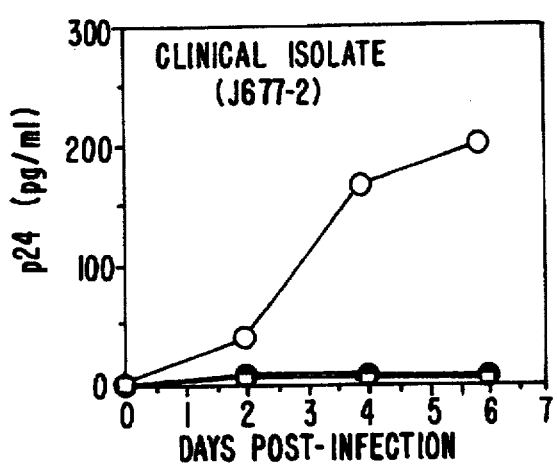
Figure 8D:
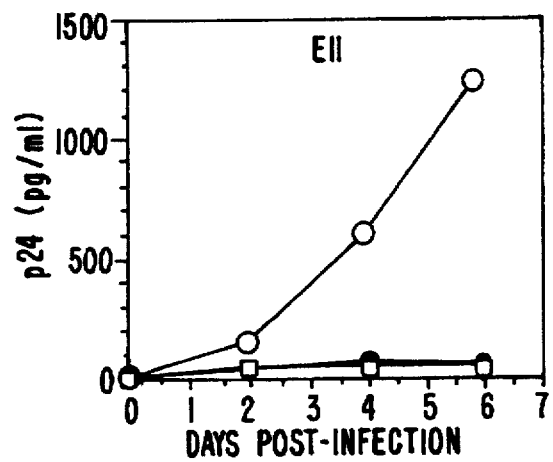

Ribozyme Expression in Stable T-Cells Lines Inhibits Infection by Diverse HIV Strains. A key consideration in developing anti-HIV therapy is to ensure efficacy against a broad spectrum of virus isolates. The target sequence identified in the hairpin ribozyme used here is highly conserved among North American/European and African isolates. Only the MN stain has one base substitution in this sequence (Myers et al., supra). The expression of p24 antigen from cloned HXB2, MN SF2 and Eli DNA was inhibited in HeLa cells transiently cotransfected with the ribozyme gene. However, transient co-transfection can not be used to evaluate the inhibition effect on uncloned isolate which is more relevant. To confirm and extend this observation to virus infection of human T cell lines, infectious virus derived from HXB2, MN, Eli as well as an uncloned clinical isolate J677-2 was used to infect JMJF-1, JMJT and JLNL-6 cells. J677-2 was obtained directly from patient's peripheral blood mononuclear cells (PBMC) by co-cultivation with normal PBMC and passaged once on MT-4 cells for amplification. The expression of p24 antigen in culture supernatant of cells infected by all the HIV-1 strains, including the clinical isolate, was drastically reduced (FIG. 8). During the culture period of 6 days, replication of MN, which contained a one-base mismatch in the target sequence, was also completely inhibited. To determine whether virus inhibition was target sequence specific, a highly replicative (HIV-2 KR) and HIV-1 HXB2 were used in parallel to infect MMJF-1, MMJT and MLNL-6 cells. As shown in FIG. 9, the expression of HIV-2 KR was not inhibited at all in the ribozyme expressing cells while HXB2 replication was again completely abolished. These results indicate that the hairpin ribozyme directed at the conserved leader sequence of HIV-1 is effective in inhibiting diverse HIV-1 strains, including an uncloned virus that has not been adapted for T-cell lines in the laboratory, but does not affect HIV-2, which contains an extensively diverged sequence in that region. The effect of the ribozyme was also apparent on syncytia formation induced by HXB2 and MN in MLNL6 and MMJF-1 cells on day 9 after infection (see FIG. 10). Both viruses induced large syncytia in the control cells transduced with vector alone, but little or no syncytia were observed in the ribozyme expressing cells.

TABLE I

Infectious Virus Titers (TCID$_{50}$) and p24 Antigen Levels in Culture

| Virus Strain | Cell Line | Days after infection | TCID$_{50}$/ml | p24 (pg/ml) |
|---|---|---|---|---|
| HXB2 | JLNL6 | 17 | $10^{4.25}$ | 813000 |
|  | JMJF-1 | 0 | — | <15 |
|  |  | 17 | ND | 887 |
|  |  | 35 | $10^{1.25}$ | 1462 |
|  | JMJT | 0 | — | <15 |
|  |  | 17 | ND | 163 |
|  |  | 35 | ND | 104 |
| MN | JLNL6 | 13 | $10^{4.00}$ | 731000 |
|  | JMJF-1 | 0 | — | <15 |
|  |  | 13 | $10^{1.25}$ | 1810 |
|  |  | 23 | $20^{2.75}$ |  |
|  | JMJT | 0 | — | <15 |
|  |  | 13 | ND | 948 |
|  |  | 23 | — | — |

The infectious titer (TCID$_{50}$) and p24 antigen of the culture supernatants in JLNL6, JMJF-1 and JMJT cells infected with HIV-1 HXB2 or MN strains on the day indicated were determined. ND, not detectable; —, not done.

Ribozyme expression confers long-term inhibition of HIV expression. JLNL6, JMJF-1 and JMJT cells were infected with HXB2 or MN. The level of RT activity in the supernatants of JLNL6 cells infected with HXB2 or MN peaked on day 19 or day 13 postinfection, respectively (FIG. 11). Thereafter the RT activity was decreased, and these control cultures were concluded because of the extensive cytopathic effects of the virus. The RT activity in HXB2-infected JMJT cells was notably suppressed to background levels up to 35 days after infection, whereas that of the HXB2 infected JMJF-1 was reduced to less than 1% of the peak RT activity in the control cells (FIG. 11). No infectivity was detected in the supernatant of JMJT on both days 17 and 35, whereas low infectivity ($10^{1.25}$ TCID$_{50}$/ml) was detected in JMJF-1 on day 35, which was still three logs lower than the TCID$_{50}$/ml of the supernatant from JLNL-6 cells on day 17 (TABLE I). Low p24 antigen levels were detectable in JMJT supernatants on days 17 and 35 (TABLE I). In MN-infected JMJT and JMJF-1, the RT activity was suppressed to less than 2% and 5%, respectively, up to 27 days after infection when compared with the peak value in MN-infected JLNL6 (FIG. 11). Infectious virus was also recoverable on days 13 and 23 in the JMJF-1 culture (TABLE I). To determine if the emergent RT activity was due to non-sustained expression of the ribozyme during the culture period, the RNA in the MN-infected JMJT and JMJF-1 cells collected on day 23 postinfection was examined by RT-PCR using ribozyme-specific primers (FIG. 11, inset).

Figure 6A:
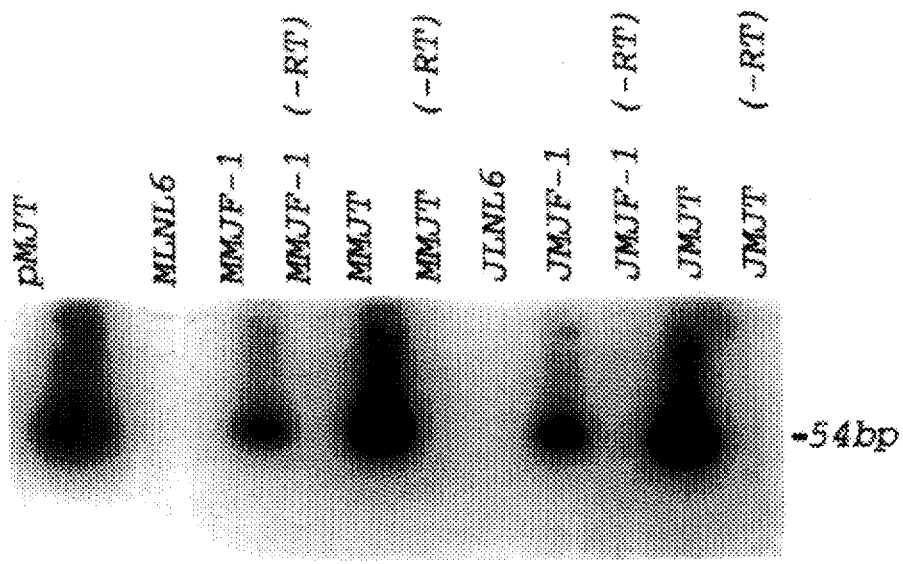
FIGS. 6A and 6B show expression of the HIV-1 specific ribozyme in stable cell lines 11 weeks (FIG. 6A) and 25 weeks (FIG. 6B) after transduction. Total RNA from the stable cell lines was extracted by the method of acid guanidinium thiocyanate-phenol/chloroform extraction using the method of Chomczynski, P and Sacch, N. *Anal. Biochem.* 162:156 (1987), incorporated herein by reference. One µg of the total RNA after treatment with RNase free DNase (RQ1 DNase:Promega) was used as template for the reverse transcription. The PCR combined with reverse transcription was carried out (94° C. for 1 minute, 42° C. for 1 minute, 72° C. for 1 minute: 30 cycles) with a primer pair of Rib4 (5'-CAC, ACA, ACA, AGA, AGG-3') (SEQ ID No. 1) and Rib2 (5'-TAC, CAG, GTA, ATA, TAC, CAC-3') (SEQ ID No. 2) according to the method of Yamada, O. et al. *J. Virol.*
Figure 6B:
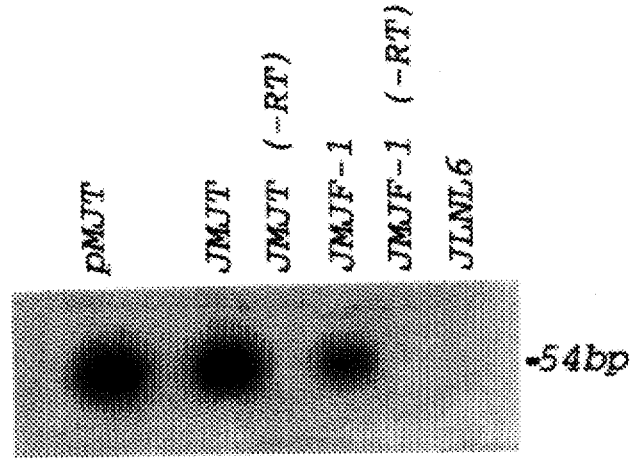

Significant levels of ribozyme RNA were detected in both JMJT and JMJF-1 cells, consistent with the cells prior to virus challenge (FIGS. 6A and 6B). Since the RT-PCR was not designed to be quantitative, the level of ribozyme expression in the stable cell lines 23 days after infection cannot be compared with the level before infection. Therefore, there remained the possibility that the level of the ribozyme expression decreased below the threshold of protection during the long-term culture. However, the ribozyme RNA was not detected in the stable cell lines even 25 weeks after transduction, as shown in FIG. 6B. The lesser inhibition of MN by the ribozyme suggests that the single base substitution in the target sequence does have an effect on ribozyme activity in long-term culture.

Test for Escape Mutants. To determine whether the infectious virus that was recovered after long term culture of JMJF-1 cells infected with HXB2 or MN (shown in FIG. 11 and TABLE I) represented escape mutants now resistant to the ribozyme, the culture supernatants from day 23 (MN) and on day 35 (HXB2) from JMJF-1 cultures were used to rechallenge JLNL6, JMJF-1 and JMJT cells. The level of p24 antigen in the culture supernatants was monitored during the culture period of 6 days. As in the primary infections (FIGS. 8, 9 and 11), the level of p24 antigen expression was greatly inhibited for both recovered viruses (FIG. 12). Therefore, the expression of low level of virus after long term culture of the infected cells was not a consequence of specific mutations that rendered the virus insensitive to the ribozyme. Rather, the gradual increase in the amount of viral RNA may eventually titrate out, at least in part, the antiviral effect on the ribozyme.

The Ribozyme Also Inhibits Early Events in Virus Replication. It has been observed that transient co-transfection of viral DNA and ribozyme gene led to reduction of virus RNA and protein production demonstrated that the ribozyme inhibited virus gene expression, presumably by cleavage of the transcribed viral mRNA. Moreover, since the viral genomic RNA also contained the target sequence, the ribozyme can potentially cleave the incoming viral RNA and prevent the establishment of integration as well.

To examine if the ribozyme indeed interfered with early events of virus replication, proviral DNA synthesis was measured 18 and even 6 hours after infection with HIV-1 in cells with and without expression of ribozyme, using a semi-quantitative, nested double PCR procedure as follows. The amplification of HIV-1 LTR derived sequences in cellular genomic DNA from JMJT and JLNL6 cells at 18 hours after infection with HXB2 at an input M.O.I of 0.1 was first carried out with a primer pair for HIV-1 LTR [SK29 (Ou, C-Y et al., Science 239:295 (1988) incorporated herein by reference) and GK2] for 30 cycles. As an internal control, a primer pair for β-globin gene [PC03 and GH21 (Saiki et al., Science 239:487 (1988), incorporated herein by reference)] was added to the reaction tubes after the 10th cycle of the first PCR to avoid potential interference of β-globin product with the amplification of LTR sequences, since the amount of β-globin DNA was estimated to be higher than that of HIV-1 DNA in the cellular extracts due to low percentage of infected cells.

For the 2nd PCR, 1/10th volume of the 1st PCR product was added and the amplification was carried out (30 cycles) with primer pairs SK29/30 (Ou, C-Y et al., supra) for HIV and RS06/GH21 (Saiki et al., supra)/GH21 for β-globin. Ten μl each of the PCR product of the 2nd PCR was collected at every 5 cycles and the amplified products were detected by gel-electrophoresis and Southern blot analysis. Neither the β-globin product nor the HIV-1 LTR product, which contained the target sequence of the ribozyme, was detectable in extracts of JMJT and JLNL6 by gel-electrophoresis and staining with ethidium bromide after the first PCR. In the second PCR, β-globin product was detected for both JMJT and JLNL6 at amplifications of 10 cycles or higher. Since there was no significant difference on the intensity of the signals of β-globin products hybridized with a $^{32}$P-labeled probe between JMJT and JLNL6, the efficiency of amplification was considered to be similar between these two samples (FIG. 12). The HIV-1 LTR products amplified in the same reaction tube as the β-globin product were first detected at the 15th cycle and the 25th cycles for JLNL6 and JMJT, respectively (FIG. 16). To estimate the relative amounts of HIV-1 DNA in the cellular DNA extracts, different concentrations (0.05 fg to 500 fg/μl) of HIV-1 SF2-containing plasmid DNA was amplified using the same primers and conditions. Detection of the HIV-1 LTR products at 15th and 25th cycles corresponded to 50 fg and 0.5 fg plasmid DNA, respectively. Therefore, JMJT contained approximately 50–100 times less HIV-1 DNA than JLNL6 at the same input of cellular DNA. The same result was obtained when JMJT and JLNL6 cells were examined 18 hours after infection with HXB2. This result shows that the ribozyme also efficiently interfered with early events in viral replication, presumably by cleaving incoming viral RNA.

Ribozyme Gene Therapy Against HIV. It has been shown, above, that a hairpin ribozyme targeting the 5' leader sequence of HIV-1 inhibit virus expression from several HIV proviral DNA clones by transient co-transfection into HeLa cells. Furthermore, the inhibition was shown to be primarily due to the catalytic, not antisense, property of the ribozyme, since a disabled ribozyme was only about 10% as effective. T-cell lines stably expressing this ribozyme gene exhibited long term (for the duration of the experiment, which was 35 days) resistant to HIV-1 infection.

One unique feature of the ribozyme approach is that it can target multiple steps of the retroviral replication cycle: the genomic RNA of the incoming virus after uncoating, the viral mRNA transcripts and the genomic RNA to be packaged into the progeny virions. Each can be a substrate for cleavage by the ribozyme. Co-transfection of the ribozyme gene and proviral DNA clones has also been shown herein to result in significant (up to 95%) reduction of viral RNA and protein expression, establishing that the ribozyme was effective in blocking virus expression from pre-existing proviral DNA. However, later experiments showed that the synthesis of proviral DNA in a one round infection also was reduced by approximately 100 fold in cells expressing the ribozyme. Thus, the ribozyme was effective in blocking the establishment of virus infection.

It was also of interest to note that Jurkat cells transduced with the leader sequence specific ribozyme often had no detectable infectious virus even though low levels of p24 were found in the supernatant (TABLE I). Therefore, it can be noted that the ribozyme can further decrease the relative production of infectious virions by cleavage of the packaged progeny RNA.

The above methods and constructs can be used in combination with other AIDS therapies for greater synergy of anti-viral effects. For example, therapies that block the establishment of infection can be combined with approaches that block the production of virus from infected cells. Thus, the ribozyme stands unique as a single-agent combinatorial regimen.

It also has been shown that the ribozyme is effective against diverse strains of HIV-1, including a Zairian strain (ELI) and an uncloned clinical virus isolate. The target sequence is completely conserved among known HIV-1 sequences. A single exception is MN, which contained a one-nucleotide substitution at position 6 distal to the CUG cleavage site (see Myers et al., supra). Indeed, expression of MN was inhibited less completely, although still to a significant extent. The exception in MN raised the concern that virus escape mutants could be generated rapidly in the presence of the ribozyme by single-site mutations. However, at least for the duration of the experiment, there was no evidence that escape mutants were generated with high frequency. The virus recoverable from both HXB-2 and MN infected cells after long term culture still exhibited exquisite sensitivity to ribozyme inhibition.

Experiment No. 3

Transduction of Human Peripheral Blood Lymphocytes (PBL) with retroviral vectors. The feasibility of using retroviral vectors to transduce human peripheral blood lymphocytes (PBL) also was tested. This is not only of significance for studying the efficacy of the ribozyme in human primary T cells; it is also important for the reason that PBL system is ideal for studying the ribozyme effect on the replication of HIV clinical isolates. In addition, this model is predictive of success in using HIV ribozymes gene therapy in the HU-PBL-SCID mice model.

Under stimulatory conditions, lymphocytes proliferate and can be transduced by retroviral viral vector encoding the neomycin resistance gene (see, for example, Fauser, A. A. et al, *J. of Cell. Biochem.* 45:353–358 (1991), incorporated herein by reference). Non-transduced PBMCs can then be eliminated by culture in the presence of the antibiotic G418. It is possible for the resistant recombinants to be expanded as much as 1000 times if maintained in IL-2 supplemented media, Culver, K. W. et al. *Transplantation Proceedings* 23:170–171 (1991), incorporated herein by reference.

Human PBMCs (without depletion of macrophages from peripheral blood lymphocytes) were transduced with the retroviral vectors pMJT, pMJF-1 and pLNL-6 using the following conditions. Ficoll-hypaque purified PBMCs were resuspended in RPMI+10% FCS+PHA-P for 2-3 days. After activation, lymphocytes were continuously maintained in IL-2 (20 U/ml)-supplemented medium. Stimulated cultures were either incubated with supernatants or co-cultivated with PA317 cell lines producing the different retroviral vectors. Following three days of transduction, recombinants were selected in G418 (400 µg/ml) IL-2 (20 U/ml)-supplemented medium for 8–9 days. From 1×10$^6$ initial PBMCs, approximately 2×10$^6$ G418 resistant recombinants were generated. LNL-6 and MJT transduced cultures were designated TLNL and TMJT respectively. Viability of transduced/selected cultures was not adversely affected by the presence of ribozyme as determined by comparison of TLNL vs. TMJT cell growth over a 16 day period. Infection of the surviving PBMC with HIV-1 (HXB2) showed greatly reduced virus production in the ribozyme transduced cells, while cells transduced with the control vector (LNL-6) were productively infected.

Experiment No. 4

Transfer of an anti-HIV-1 ribozyme gene into primary human lymphocytes

In order to more closely simulate the in vivo infection process for investigations of anti-HIV-1 ribozyme gene therapy, a system was developed to transfer ribozyme genes into freshly isolated human peripheral blood lymphocytes (PBLs) using a murine retrovirus vector. Following transduction and G418 selection, human PBLs from multiple donors expressed the ribozyme and resisted challenge by HIV-1 viral clones and clinical isolates, while control vector-transduced PBLs remained fully permissive for HIV-1 infection. No inhibition of an HIV-2 clone lacking the target was seen in ribozyme-expressing PBLs. Ribozyme expression had no effect on viability or proliferation kinetics of the primary lymphocytes. This study is the first demonstration in primary human T cells of resistance to HIV-1 infection conferred by gene transfer.

Vector Preparation. Retroviral constructs pLNL-6 (control vector) and pMJT (ribozyme vector) were transduced using amphotropic PA317 retroviral vector producer cell lines made by standard methods described above. Retroviral vector containing supernatants were harvested from producer lines, filtered and stored at −80° C. Titers were determined on 208F cells.

Transduction and Selection of PBLs. Peripheral blood mononuclear cells (PMCs) were isolated from various donors by venipuncture followed by ficoll-hypaque density centrifugation. Lymphocytes were maintained at a density of 1–3×10$^6$ cells/ml in RPMI+10% FCS, 20–100 U/ml IL-2, 100 units/ml penicillin and 100 µg/ml streptomycin. Proliferation was stimulated by addition of anti-CD3 antibody, OKT3 (Ortho Diagnostics) (5 ng/ml) on the day of ficoll purification.

Two to three days after initiating OKT3 stimulation, the media was replaced with filtered packaging line supernatants containing 4 µg/ml protamine sulfate (M.O.I.=0.5–2.0). After 4–6 hours, lymphocytes were returned to the original (IL-2 and OKT3-containing) media and incubated overnight. This transduction procedure was repeated daily for 2–4 days. G418 (400 µg/ml active) was added to cultures 24 hours after the final transduction. Cultures were maintained under selective conditions until untransduced control cultures were completely killed, approximately 8–11 days. In some cases, dead cells were removed by ficoll density centrifugation. CD4/CD8 surface marker determinations were performed by flow cytometry (Cassel et al., *Exp. Hematol.* 21:585 (1993), incorporated herein by reference).

HIV challenge. G418-selected cultures were incubated with HXB2, clinical isolates or HIV-2 KR at a M.O.I. of 0.01, overnight and washed twice. HIV-1 clinical isolates were derived by incubation of PBLs from HIV-seropositive individuals in media containing IL-2 followed by a single passage in the MT4 cell line. During challenge, lymphocytes (1×10$^6$ cells/ml, 0.2 ml total volume) were maintained in RPMI 1640 supplemented with 20 U/ml IL-2 (without G418) and samples taken every 2–3 days. HIV production was monitored by either p24 or p26 ELISA (Coulter).

RESULTS

Selection and characterization of transduced PBLs. PBMCs obtained from several donors were stimulated with anti-CD3 antibody and transduced with 2 amphotropic vectors in parallel: MJT, which encodes the 5' leader sequence specific ribozyme transcribed by RNA polymerase III, and control vector LNL-6 (FIG. 16A). These cultures were then subjected to selection of transductants based on their resistance to G418. Resistance is conferred by the LTR driven neomycin phosphotransferase gene (NPT II) which is present in both constructs. Untransduced cultures were completely killed within 8–11 days, whereas LNL-6 or MJT transduced cultures were able to survive under these conditions. Freshly isolated PBLs could reproducibly be maintained for up to 5–6 weeks in culture under the conditions described above.

Anti-HIV ribozyme is Expressed in G418-selected PBLs. Expression of the 5' leader sequence ribozyme was detected by subjecting total RNA from selected cultures to reverse transcription followed by PCR (FIG. 17). Since the LTR and tRNA driven transcripts are encoded on opposite strands of integrated vector DNA, pol III initiated ribozyme RNA can easily be distinguished from the LTR-neomycin phosphotransferase transcript by the use of a ribozyme-specific primer during the RT step of the PCR protocol. Elimination of the reverse transcriptase from the procedure resulted in no detectable product, indicating that only DNA derived from reverse-transcribed RNA template was amplified.

Characteristics of G418-selected PBLs. Comparison of the growth kinetics of selected cultures of LNL-6 and MJT transduced lymphocytes showed that expression of the ribozyme did not significantly influence the viability or proliferation of these cells (FIG. 18A). Viability and growth of the transduced cells required the presence of exogenous IL-2 regardless of the transducing vector. The phenotypes of the transduced and selected cultures also were compared in terms of their CD4/CD8 ratios (FIG. 18B). Although some variability was seen in these cell surface markers from donor to donor, the distribution of CD4 and CD8 cell populations was not different for the ribozyme or control vector transduced cells.

Figure 19A:
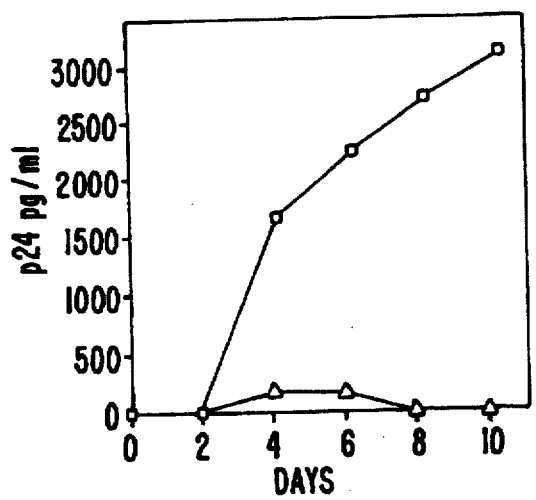
Figure 19B:
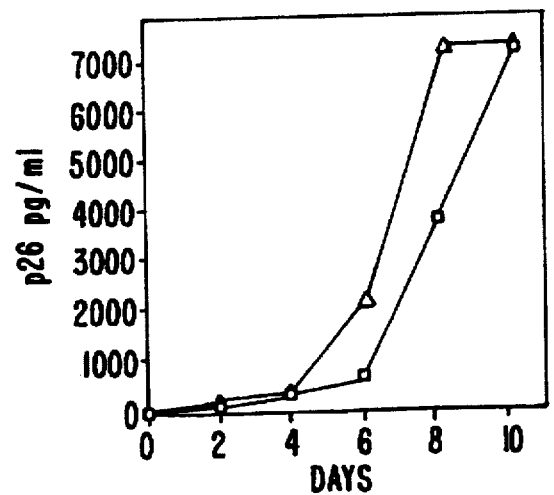
Figure 19C:
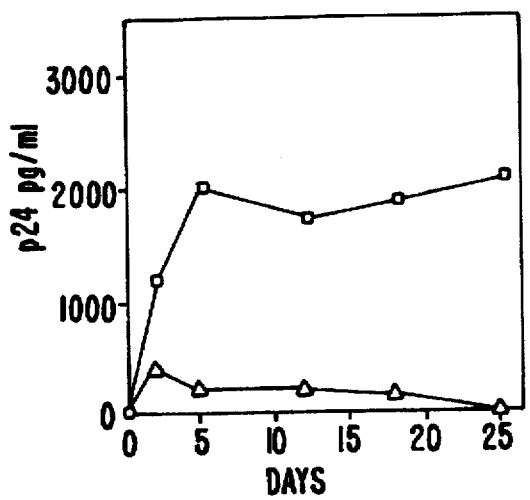

Long Term Protection of Ribozyme expressing PBLs from HIV Infection. G418-selected cultures were challenged with EXB2, and HIV-1 viral clone that contains a fully conserved HIV 5' leader sequence ribozyme target sequence. Compared on day 10 post infection, HIV production was inhibited in the MJT transduced cultures by a factor of one thousand fold, relative to the LNL-6 transduced cultures (FIG. 19A). To ensure that the observed inhibition was not merely due to the selection of a culture that was no longer infectable for other reasons (e.g. down-regulation of the cell surface receptor, induction of interferon, etc), cultures also were challenged with HIV-2, which contained a completely diverged sequence at the target site. As shown in FIG. 19, infection with HIV-2 resulted in equivalent productive infection in both LNL-6 and MJT-transduced PBLs, indicating that viral inhibition was target sequence specific. Since cytopathic effects are not observed in PBL cultures, regular additions of rIL-2 (20 U/ml) allowed HIV-challenged lymphocytes to be maintained for several weeks. Viral replication was repressed throughout this period (FIG. 19).

Figure 19D:
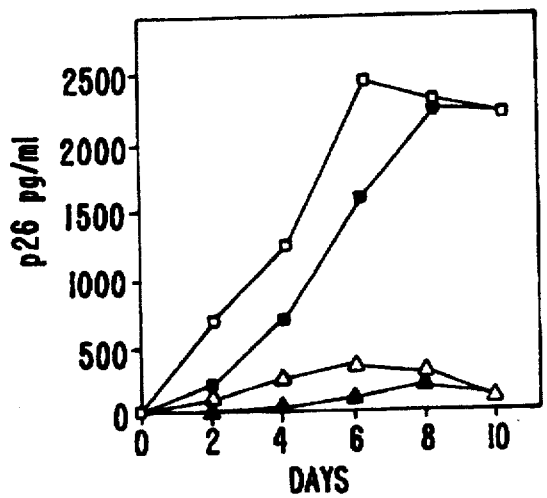

Protection Extends to Clinical Isolates. For clinical applications, an anti-HIV gene must confer resistance to a broad spectrum of HIV-1 strains that are found naturally in the human population. Therefore, the investigators have gone beyond laboratory HIV isolates to include clinical isolates of HIV-1 to challenge transduced and selected lymphocytes from various donors. FIG. 19D shows effective inhibition of infection by two clinical isolates in ribozyme transduced PBLs obtained from two different donors.

Experiment No. 5

Intracellular immunization of human hematopoietic stem/progenitor cells with a ribozyme against HIV-1

In this study, the previous protocols were followed for enrichment of CD34+ cells and for retroviral transduction (Lu, M., et al., *Human Gene Therapy* 5:203 (1994); Smith, C., *J. Hematotherapy* 1:155 (1992); Cassel, A., et al., *Exp. Hematol.* 21:585 (1993) each incorporated herein by reference). However, the LNL6 based vectors contained the ribozyme gene under the control of internal pol III promoters, which ensures higher and more persistent gene expression compared with pol II promoters. These vector constructs are shown in FIG. 20A. Two pol III promoters were used: tRNA$_{val1}$, a house-keeping cellular gene promoter, and the adenovirus VA1, a strong viral promoter. Human fetal cord blood was used as the source of CD34+ cells for several reasons: high transduction efficiency of cord blood derived progenitor cells, higher proportion of stem/progenitor cells in cord blood relative to adult bone marrow, and higher potential for proliferation and self-renewal for cord blood stem cells versus bone marrow cells. Furthermore, cord blood derived stem cell gene therapy for infants is logistically less problematic, and potentially could be extended to HLA-matched adults in allogeneic transplantation settings.

Two $(2)\times10^5$ purified CD34+ stem/progenitor cells were prestimulated with growth factors, SCF (Stem cell factor, 25 ng/ml), IL-3 (500 U/ml), and IL-6 (500 U/ml) for 24 hours, and infected with cell-free recombinant virus MJT or MJV, as well as the vector LNL6 produced from cloned PA317 producing cell lines with an M.O.I. of 1 to 5 (virus titered on 208F cells). See legend to FIG. 20A. To do so, equal volume of supernatant of virus was added to the cells and incubated for 16–24 hours in the presence of 4 µg/ml polybrene. After washing, cells were returned to the culture medium containing SCF, IL-3, and IL-6 at the concentrations mentioned above and incubated for 48–72 hours. Clonogenic assays were performed in the absence of G418. Colonies were picked from each plate and nested DNA PCR using neo gene primers was performed to determine transduction efficiency. High transduction efficiency (80–100%) was reproducibly obtained. Ribozyme expression in these progeny cells was assessed by RNA PCR using ribozyme-specific primers. The specificity of the PCR products was confirmed by dot-blot using a third ribozyme-specific probe. As shown in FIG. 20, in all the colonies derived from transduced stem/progenitor cells, both internal pol III promoters supported ribozyme expression (MJT and MJV); no signal could be detected in LNL6-transduced cells, or non-transduced stem/progenitor cells (d1 and d2).

Furthermore, no signal could be detected when RT was omitted from PCR procedure in the ribozyme-transduced cells (d3–d5 MJT; d4–d8 MJV), confirming that RNA rather than DNA signals were detected. The variable levels of ribozyme expression in the positive samples may be partly due to the different sizes (number of cells) of the colonies picked. As positive controls, $2\times10^3$ MJT transduced Jurkat cells (d9 and d10) were used, which were shown to completely resist HIV-1 infection. Relative to these cells, the progeny of the transduced CD34+ cells colonies (each containing only 100–500 cells) appeared to express high levels of ribozyme, although the assay was only semi-quantitative.

Since MMLV based retroviral vectors can only infect dividing cells, pre-stimulation of the stem cells with a combination of cytokines before transduction was routinely employed. During this process, some CD34+ stem cells would differentiate into more committed progenitor cells, which still might maintain colony forming capacity. To address the question of whether the population of CD34+ stem cells, rather than merely more committed progenitors, could be transduced with high efficiency, flow cytometry was used to re-separate the CD34+ cells after the pre-stimulation and transduction. About 25% of the total cell population remained CD34+. CD34+ single cells were then sorted into 96-well plates and cultured in IMDM medium with 10% FCS. In addition to SCF (25 ng/ml), IL-3 (500 U/ml), and IL-6 (500 U/ml), GM-CSF (500 U/ml) was added to the culture medium. Colonies comprising 300–500 cells were derived from single cells in liquid culture in some wells in a period of two weeks (colony efficiency is about 30%). Nested DNA PCR using neo primers described above showed that a transduction efficiency of 80–100% was also obtained for this cell population. Hence, there was no detectable difference in the transduction efficiency of the CD34+ cell population and of the overall cell population.

The ultimate goal of gene therapy targeting autologous or allogeneic stem cells for HIV infection is to reconstitute the immune system with genetically altered, HIV resistant cells. However, the foremost requirement is that transduction and/or transgenes expression would not curtail the capacity of the stem cells to differentiate into multiple cell lineages.

Clonogenic assays and progeny phenotyping assessments were performed to address this important issue. Untransduced stem cells were cultured under the same conditions, except that culture media was used in place of infectious virus during transduciton. As shown in TABLE II, equivalent numbers of cells with different lineages were obtained for untransduced cells and those transduced with control or ribozyme vectors. Therefore, neither retroviral transduction nor ribozyme expression had any impact on stem cell differentiation. An equally important question is whether transduction and ribozyme expression would change the total stem cell colony forming efficiency. As shown in FIG. 21, there is also no significant difference of colony forming efficiencies among ribozyme-transduced stem cells and vector control-transduced stem cells (compare the last three columns), suggesting that ribozyme expression had no apparent adverse effect on the progenitor capacity of the stem cells. Transduction itself reduced little, if at all, the colony forming efficiency of the stem cells (FIG. 21).

TABLE II

|         | Un-Tran  | LNL6     | MJT      | MJV      |
|---------|----------|----------|----------|----------|
| CFU total | 196 + 43 | 156 + 48 | 158 + 48 | 151 + 38 |
| BFU-e   | 74 + 73  | 60 + 52  | 68 + 72  | 72 + 89  |
| Mix     | 1 + 1    | 2 + 1    | 1 + 1    | 2 + 2    |
| Total   | 271 + 63 | 218 + 6  | 227 + 34 | 225 + 63 |

Clonogenic assay and progeny phenotyping of the retroviral vector-transduced stem cells. 48 hours after retroviral transduction, $0.5 \times 10^4$ transduced- or untransduced-stem cells were mixed with Iscove's Modified Dulbecco Medium (IMDM, GIBCO) containing 20% FCS, 1.2% methylcellulose, 26 ng/ml SCF, 500 U/ml IL-3, 500 U/ml IL-6, 5 ng/ml GM-CSF, 2.5 U/ml erythropoietin and $5 \times 10^{-5}$ M2-mercaptoethanol. The cultures were plated in duplicates and incubated for 14 days at 37° C. in 5% $CO_2$ in a humidified atmosphere. Each colony consists of more than 50 cells. The granulocyte-macrophage colonies (CFU-GM) and erythroid bursts (BFU-E) are identified by their morphology under the microscope. Each number of colonies represents three identical experiments using stem/progenitor cells isolated from cord blood of independent donors.

To assess the in vitro efficacy of the ribozyme gene, the progeny cells derived from the transduced stem/progenitor cells were examined for resistance to HIV challenge. In HIV infected individuals, the major viral targets are CD4+ T-lymphocytes and macrophages/monocytes. Attempt to promote differentiation of the transduced stem/progenitor cells into lymphocytes with different combination of cytokines and growth factors was not successful. However, adherent monocytes/macrophages were successfully obtained using the experimental conditions described in the legend to FIG. 22A. G418 was not included in the media during the cell culturing process, since it was reported that neo gene expression in LNL6 vector was not persistent, Lu, M., et al., (1994), supra., and since high efficiency of transduction and ribozyme expression was already observed in our system. These cells were not infectable by HIV-1/HXB2, a lymphotropic strain but could be productively infected by HIV-1/Bal, a macrophage tropic strain. These cells were challenged with HIV-1/Bal to determine if the progeny macrophage cells derived from the ribozyme transduced stem/progenitor cells would be protected from HIV-1 infection. As shown in FIG. 22A, both MJT and MJV transduced cells had significantly reduced HIV-1 replication up to day 6, compared with control vector LNL6 transduced cells (cell cultures were terminated thereafter). Greater inhibition was observed in stem cells transduced by MJV than MJT (FIG. 22A). These data were reproduced with stem/progenitor cells isolated from a different donor. The inhibition was unlikely caused by differences in cell viability, since LNL6, MJT, and MTV exhibited similar growth kinetics under these liquid culturing conditions before virus challenge (see growth curves in FIG. 22B). RT-PCR was performed to determine if expression of ribozyme was maintained in these progeny cells to account for the observed inhibition of virus replication (FIG. 22C). Ribozyme expression was detected in MJT and MJV transduced cells (lanes 3 and 6), but not in LNL6 transduced cells (lane 1) at about two months after the transduction. Again, there is no signal detected when RT was omitted in the reaction (Lanes 4 and 7) indicating that specific RNA rather than DNA was detected. There was no significant difference between the levels of ribozyme expression by MJT and MJV, so it is not clear why greater inhibition was observed in MJV-transduced stem cells. Since the ribozyme expression cassettes were constructed in an antisense orientation with regard to LTR (FIG. 1), differentiated transcription can be obtained from pol III and pol II (MMLV LTR) promoters by using one of the two primers in the reverse transcription step. Stronger signals were detected for the pol III transcripts (lanes 3 and 6) than for the pol II transcripts (Lanes 2 and 5, see legend for detail). This is consistent with the observation of low neo gene expression from the LTR in hematopoetic stem cells. The low levels of virus expression might have resulted from the small portion of untransduced cells since G418 selection was not performed. However, short term G418 selection could be imposed after transduction to ensure more complete protection from HIV-1 infection. The data presented here represent, to Applicants' knowledge, the first report of in vitro efficacy for intracellular immunization of the macrophage/monocytes cell population.

In summary, these results show that intracellular immunization of hematopoietic stem/progenitor cells with a ribozyme against HIV-1 is feasible as a gene therapy approach for the treatment of HIV infection. An appropriate target population for stem cell gene therapy may be HIV-1 positive newborns. One can use the ex vivo procedure to transduce stem cells isolated from cord blood with the ribozyme gene and reinfuse the genetically-altered stem cells into the patients after their positive HIV status is verified. It was reported that 25% of infants born to HIV positive mothers are indeed infected with HIV. There are advantages for initiating the gene therapy at the time of birth or as soon as possible thereafter, before significant viral damage has been done to the thymic and lymphoid organs, since successful immune reconstitution, especially of the T-cells, by the genetically altered stem cells will essentially depend on the normal functions of these organs. Since pediatric AIDS progresses more rapidly than the adults disease (80% infected infants become symptomatic in the first year), in vivo gene therapy efficacy can be assessed more rapidly in this population. The issue of whether CD34+ cells can be infected by HIV is still controversial, but it is generally agreed that the majority of CD34+ stem cells is not infected. These results show that CD34+ cells can be transduced with the ribozyme gene, which inhibits both the establishment of infection and virus expression; thus, the ribozyme gene therapy using stem cells as targets can be a promising preemptive strategy for the treatment of HIV infection.

Transduction of human CD34+ stem cells with the ribozyme. The use of long-term repopulating hematopoietic stem cells for gene therapy against AIDS would be ideal because they are capable not only of self-renewal but also of differentiation into HIV target cells. We recently developed a method in which CD34+ cells can be transduced with an efficiency of up to 90%. Purified stem cells were infected separately with cell-free recombinant virus MJT, MJV, and LNL-6 (FIG. 1) in the presence of 4 μg/ml polybrene. Transduction efficiency was determined by PCR of stem cell derived colonies grown in semi-solid agar.

Experiment No. 6

Transduction in the HU-PBL-SCID mouse model. The hu-SCID mouse is a human/mouse chimerae created by injecting human peripheral blood leukocytes into the peritoneal cavity of SCID mice. Koch, J. A. and Ruprecht, R. M. *Antiviral Res.* 19:81–109 (1992). Phenotypically and functionally normal human lymphocytes can be isolated from the blood and lymphoid tissues of the chimerae. These mice can be infected with HIV-1 reproducibly with both laboratory isolates and laboratory-adapted strains.

Primary PBL are transduced with retroviral vector containing nucleic acid encoding HIV specific catalytic ribozyme. Following transduction and selection, PBL are then injected intraperitoneally (IP) into severe combined immunodeficiency (SCID) mice ($2 \times 10^7$ cells/mouse) and two days later challenged with HIV, preferably HIV-1. Thirty days post-challenge, the animals are sacrificed and cells are isolated from the peritoneum and spleen. Viral infection and production will be detected using p24 ELISA in blood samples collected at different time intervals. Alternatively, these samples will be used to co-cultivate with fresh PBLs for virus isolation and or for HIV gag PCR to determine virus load. In addition, depletion of CD4+ T cells will be determined by FACS.

Clinical Trial. HIV seropositive individuals are treated with autologous T cells transduced with a retroviral vector containing a nucleic acid encoding an HIV-specific catalytic ribozyme. Peripheral blood lymphocytes are collected by apheresis and enriched for CD4 cells by negative selection. The enriched cells are stimulated in culture and subsequently transduced with the retroviral vectors. Separately, part of the cells can be transduced with a marker vector for survival comparison. After infection with retrovirus carrying the ribozyme, the cells are selected in G418. The transduced cells are expanded under culture conditions that limit the spread of endogenous HIV. The genetically modified cells are mixed and reinfused into the donor.

To assess efficacy, the participants' functional immune status, plasma viremia, p24 antigen levels, percentage of HIV-infected peripheral blood cells and the relative survival of retroviral transduced cells versus control cells are followed.

Eligibility Criteria. Patients selected for treatment with the invention are preferably positive for HIV by ELISA or Western Blot, and demonstrate plasma viremia and measurable p24 antigen. Their CD4 count is preferably between 200 and 600 cell/mm$^3$ and their anticipated survival is greater than 3 months. Performance status is preferably 0, 1 or 2 (see below). Patients may be further selected on the basis of nucleotide sequence determination of the ribozyme target sites present in their HIV in vivo. This will be carried out by PCR and sequencing of the appropriate target sequences directly from the patients' PBL. Those patients harboring HIV with significant target site divergence will be excluded.

| PATIENT PERFORMANCE STATUS 5-GRADE SCALE | |
|---|---|
| GRADE | STATUS |
| 0 | Able to carry out all normal activity without restriction. |
| 1 | Restricted in physically strenuous activity but ambulatory and able to do light work. |
| 2 | Ambulatory and capable of all self-care, but able to carry out any work. Up and about more than 50% of waking hours. |
| 3 | Capable of only limited self-care, confined to bed or chair more than 50%. |
| 4 | Completely disabled. Cannot carry on any self-care. Totally confined to bed or chair. |

Clinical Evaluation. All prospective patients are preferably evaluated with a complete medical history, physical examination, laboratory studies, electrocardiogram, and chest x-ray as outlined below.

A complete medical history preferably includes information covering the duration of diagnosis of HIV infection, disease manifestations, and complications; history of all known allergies; history of opportunistic infections and malignancies; history of sexually transmitted diseases including gonorrhea, syphilis, hepatitis, mononucleosis, CMV infection, herpes, and parasitic diseases; current medications, including over-the-counter preparations; history of substance abuse and recreational drug use; history of depression, anxiety, mental illness, emotional problems, use of psychiatric medications, and previous psychotherapy; knowledge and practice of "safe sex"; current contraceptive practices; and surgical procedures and results.

A complete physical examination can include patient performance status (above); weight; height; vital signs; pulmonary examination; cardiac examination; abdominal examination; neurologic examination; oropharyngeal examination; and stool guaiac.

Laboratory and other investigative studies (preferable done at screening, entry, and follow-up visits according to the schedule below) can include: CBC and differential; platelet count; reticulocyte count; urinalysis; protime (PT) and partial thromboplastin time (PTT); serum electrolytes such as NA+, K+, Cl–, HCO3–; blood glucose; blood urea nitrogen (BUN); uric acid; total bilirubin; alkaline phosphatase (if 2× upper limit of normal, then determine the gamma glutamyl transpeptidase (GTP)); aalanine aminotransferase (ALT); aspirate aminotransferase (AST); lactate dehydrogenase (LDH) and, if elevated, LDH isoenzymes; calcium, albumin, total protein, quantitative immunoglobulin; hepatitis B and C serologic screens, blood cultures for *Mycobacterium avium-intracellulare*, serum cryptococcal antigen; a lymphocyte profile; HIV polyerase chain reaction (PCR); HIV ELISA with confirmatory Western blot; serum p24 antigen; quantitative HIV cultures of plasma; β2 macroglobulin; quantitative DNA PCR of DNA extracted from peripheral blood mononuclear cells (PBMC) utilizing primers specific for both the retroviral vector and control; purified protein derivative of tuberculin (PPD) and tetanus toxoid control; and a tetanus toxoid booster.

A lymphocyte profile can include, but is not limited to: cellular phenotype of peripheral blood by FACS analysis, including CD4$^+$ and CD8$^+$ counts and percentages, in vitro lymphocyte proliferative assays including responses to mitogens (PEA, PWM, Copn-A), soluble antigens (diphtheria, tetanus, *Candida albicans*), alloantigen, and anti-CD3+/−IL2; and determination of cytotoxic cell function.

Apheresis of peripheral blood mononuclear cells (PBMC). Leudopheresis is performed either manually or using an automated cell separator. If manual techniques are used, a unit of whole blood is withdrawn with a suitable anticoagulant (such as ACD-A or heparin) and separated into components by centrifugation. The leukocytes are harvested and the remaining red cells and plasma are returned to the patient. One to 5 units of blood can be sequentially processed in this manner. Only one venipuncture is typically necessary and the procedure requires about 30 to 45 minutes to complete.

Apheresis can be accomplished using automated cell separator devices. Whole blood is withdrawn from a venipuncture site at a rate of about 50 to 60 ml/min and channeled into the cell separator where cellular and plasma fractions are separated by centrifugation. The leukocytes are harvested into a component bag, and the red cells and plasma are reinfused into the patient via a second venipuncture site. Anticoagulation is achieved using ACD-A or its equivalent at a whole blood to anticoagulant ratio of 13:1. Maximum extracorporeal blood volume ranges from about 300 ml to about 600 ml depending on the device used. One to two hours are required to process 1 to 5 liters of blood. Typically, no more than $5\times10^9$ leukocytes are removed during a single leukopheresis. The procedures are carried out so that extracorporeal volume is no more than 15% of the blood volume in adults. These volumes are calculated using standard formulae.

Hazards and Precautions for Leukopheresis. Adverse reactions to apheresis procedures are rare and include vasovagal episodes related to needle insertions and transient volume loss, and cutaneous paraesthesia related to citrate-induced hypocalcemia. The former reaction is handled by postural manipulation and fluid administration. The latter is usually relieved by slowing the rate of, or temporarily interrupting, the anticoagulant infusion. Under some circumstances there can be a minor increase in clotting parameters in the patient due to reinfusion of anticoagulated blood products, resulting in a slightly increased bleeding tendency. This effect, however, is transient and resolves with therapy.

Cell Separation and Enrichment for CD4 T Cells. Ficoll-Hypaque density gradient centrifugation is used to separate PBMC from red blood cells and neutrophils according to established procedures. Cells are washed with modified AIM-V (which consists or AIM-V (GIBCO) with 2 mM glutamine, 10 µg/ml gentamicin sulfate, 50 µg/ml streptomycin) supplemented with 1% fetal bovine serum (FBS). Enrichment for CD4 cells is performed by negative selection with anti-CD8 monoclonal antibody coupled to magnetic beads according to standard techniques. An aliquot of cells is analyzed for cell surface phenotype including CD4, CD8, CD3 and CD14.

Transduction and Expansion of CD4-enriched Cells. Cells are washed and resuspended at a concentration of $5\times10^5$ cells per ml of AIM-V modified as above and containing 5% FBS and 100 U/ml recombinant IL-2 (rIL-2) (supplemented AIM-V). In some cases, 25 nM CD4-PE40 (a recombinant protein consisting of the HIV-1-binding CD4 domain linked to the translocation and ADP-ribosylation domains of *Pseudomonas aeruginosa* exotoxin A) may be added to the cell cultures for the remainder of the cell expansion in an effort to selectively remove HIV infected cells from the culture. CD4-PE40 has been shown to inhibit p24 production in HIV-1-infected cell cultures and to selectively kill HIV-1-infected cells. Furthermore, CD4-PE40 and reverse transcriptase inhibitors exert highly synergistic effects against HIV-1 spread in human primary T cells.

To stimulate proliferation, OKT3 monoclonal antibody (Ortho Diagnostics) is added to a concentration of 10 ng/ml and the cells are plated in 24 well plates with 0.5 ml per well. The cells are cultured at 37° C. in a humidified incubator with 5% $CO_2$ for 48 hours. Media is aspirated from the cells and 1 ml of vector-containing supernatant (described below) supplemented with 5 µg/ml of protamine sulfate, 100 U/ml rIL-2, 100 U/ml penicillin, 0.25 µg/ml amphotericin B/ml and an additional 100 µg/ml streptomycin (25 nM CD4-PE40 can be added as described above).

Vector preparation and supernatant production are done under Good Manufacturing Process (GMP). For transductions, 80% of the PBMC containing wells are incubated with the retroviral vector containing the nucleic acid encoding the ribozyme and 20% with the control vector. The vector supernatant is added. This procedure is repeated 4–6 times. Eight to 16 hours following the final action, the vector supernatant is removed and the cells are cultured in supplemental AIM-V for 24 hours.

Selection with G418 to eliminate nontransduced cells is started by changing the media to AIM-V 302 with up to 1000 IU/ml of rIL-2, 40 uM DDI (to inhibit HIV replication), and 250–500 µg/ml of active G418. After 6–8 days of culture in G418 containing media, the cells are transferred to supplemented AIM-V plus 40 uM DDI (+/−25 nM CD4-PE40) and expanded to between $1\times10^8$ and $4\times10^9$ cells. The culture conditions for expansion of cells can be modified during the protocol if new cell culture techniques are developed.

Preparation of Peripheral Blood Cells for Reinfusion. Cells are prepared according to established methods. See Abrahamsen et al., *J. Clin. Apheresis* 6:48–53 (1991), Carter et al., *J. Clin. Apheresis* 4:113–117 (1988), Aebersold et al., *J. Immunol. Methods* 112:1–7 (1988), Muul et al., *J. Immunol. Methods* 101:171–181 (1987), and Carte et al., *Transfusion* 27:362–365 (1987), each incorporated herein by reference. After a period of about 2 weeks in culture, the cells should number between $1\times10^8$ and $4\times10^9$. The growth characteristics of cells may vary considerably from patient to patient. About 72 hours prior to reinfusion of the transduced cells, an aliquot is taken for analysis of phenotype, percentage of cells containing integrated vector, percentage of cells containing an integrated HIV proviurs, HIV culture and HIV p24 antigen. Samples are also taken for Gram stain, microbiologic cultures for aerobic and anaerobic bacteria, and fungal cultures. An aliquot of cells taken the day of reinfusion for identical studies. If greater than 10% of the cells are nonviable due to G418 selection, they can be removed by Ficoll-Hypaque density centrifugation.

Reinfusion of Expanded, Transduced Cells into Donors. Prior to infusion, blood samples are obtained and saved for analysis. Between $1\times10^8$ and $4\times10^9$ transduced cells are infused intravenously over 60 minutes. Vital signs and oxygen saturation by pulse oximetry are closely monitored according to the schedule below. Blood samples are obtained 5 minutes and 1 hour following infusion and saved for subsequent analysis. Leukopheresis, transduction and reinfusion are repeated every 2 to 3 months for a total of 4 to 6 treatment in a one year period. After the first treatment, infusions can be performed on a outpatient basis at the discretion of the clinician. If the reinfusion is given as an outpatient, the participant is monitored for at least 4 hours following the therapy.

Treatment of Infusion Related Reactions. If a patient develops fevers, chills, or muscle aches, he/she receives the appropriate dose of aspirin, ibuprofen or acetaminophen. Acetaminophen is used if the patient does not tolerate aspirin or ibuprofen. Development of a rash is treated initially with oral diphenhydramine. Patients who experience reactions to the infusion such as fever, muscle aches, and chills are premedicated 30 minutes prior to the future infusions with either aspirin, acetaminophen, or diphenhydramine. Meperidine is used for more severe chills and muscle aches that do not quickly respond to antipyretics and antihistamines. Cell infusion will be slowed or discontinued depending upon the severity of the reaction. In the event of a severe reaction, emergency life support measures are immediately undertaken.

Experiment No. 7

Bone Marrow Aspiration. Multiple bone marrow aspirations from iliac crests can be performed in all eligible patients under general anesthesia in the operating room. The bone marrow aspirations is approximately 1,000 ml in quantity and will be collected from the posterior iliac bones and crests. If the total number of cells collected is $<2 \times 10^8$/kg, a second pull possibly using the sternum and anterior iliac crests in addition to posterior crests can be performed. During the operation, two units of irradiated packed red cells will be administered to replace the volume of marrow taken by the aspiration.

Purification of $CD34^+$ cells. The hematopoietic progenitor and stem cells are characterized by the presence of a CD34 surface membrane antigen. This characteristic will be made use of for the purification. After the bone marrow is harvested, the mononuclear cells are separated from the other components by means of ficol gradient centrifugation. This is performed by a semi-automated method using a cell separator (either Baxter Fenwal CS3000+ or Terumo machine). The light density cells, composed mostly of mononuclear cells are collected and the cells will be incubated in plastic flasks at 37° C. for 1.5 hours. The adherent cells consist of many monocytes, macrophages and B-Cells and are discarded. The non-adherent cells are then be collected and incubated with the murine monoclonal anti-CD34 antibody (9C5) at 4° C. for 30 minutes with gentle rotation. The final concentration for the anti-CD34 antibody is 10 µg/ml. After two washes, paramagnetic microspheres (Dynal Beads, supplied by Baxter Immunotherapy Group, Santa Ana, Calif.) coated with sheep antimouse IgG (Fc) antibody are added to the cell suspension at a ratio of 2 cells/bead. After a further incubation period of 30 minutes at 4° C., the rosetted cells with magnetic beads are collected with a magnet. Chymopapain (supplied by Baxter Immunotherapy Group, Santa Ana, Calif.) at a final concentration of 200 U/ml will be added to release the beads from the CD34+ cells. The thus released CD34+ cells are cultured for 48 hours. Thereafter, transduction experiments using the retroviral vector construct as described above is performed.

Reinfusion of Genetically Engineered CD34+ Progenitor Cells. After the transduction experiment and after the corresponding quality controls (microbiology, clonogenic assays, viability tests), the genetically engineered bone marrow progenitor cells are reinfused back to the patient, preceded by the administration of diphenhydramine and hydrocortisone, as per standard protocol. See for example, Korbling, M. et al. *Blood*, 67:529–532 (1986) or Haas, R. et al. *Exp. Hematol.* 18:94–98 (1990), each incorporated herein by reference.

After reinfusion, the presence of the genetically engineered stem cells in the marrow is followed by regular examinations of the circulating blood as well as the bone marrow, initially on a weekly basis for the first four weeks. Subsequently, it is followed on a monthly basis for approximately six months.

TABLE III

MONITORING DURING THE STUDY

| | Screening | Hsp | Wk 1 | Wks 2–12 | Wk 13 | Wks 14–24 |
|---|---|---|---|---|---|---|
| Infusion | | X | Day 1 | | Day 1 | |
| Nursing Visit | | X | Day 1,2 | Weekly | Day 1,2 | Weekly |
| MD Visit | | X | Day 1 | | Day 1 | |
| Performance Status | X | X | Day 1,2 | Weekly | Day 1,2 | Weekly |
| CBC Platelet Diff. Retic. | X | X | Day 1 | Weekly | Day 1 | Weekly |
| Cong. Profile | X | X | Day 1 | Weekly | Day 1 | Weekly |
| Electrolytes | X | X | Day 1 | Weekly | Day 1 | Weekly |
| Hepatic. Renal Mineral | X | X | Day 1 | Weekly | Day 1 | Weekly |
| Quantiative Immunoglobs. | X | X | Day 1 | | Day 1 | |
| Pregnancy Test | X** | X** | Day 1** | | Day 1** | |
| Hepatitis B, C Screen | X | X | | | | |
| MAI Blood Cultures | | X | | | | |
| Serum Crypt Antigen | X | X | | | | |
| PPD & Tetanus Control | X | | | | | |
| Tetanus Toxoid Booster | X | | | | | |
| Lymphalysis | X | X | Day 1 | | Day 1 | |
| Chest X-ray | X | | | | | |
| ECG | X | X | | | | |
| HIV DNA-PCR | X | X | Day 1 | Weekly | Day 1 | Weekly |
| BETA-2-Microglobulin | X | X | Day 1 | | Day 1 | |
| Lymphocyte Profile | X | X | Daily | Weekly | Daily | Weekly |
| ELISA & Western Blot | X | | | | | |
| Serum p24 Antigen | X | X | Daily | Weekly | Daily | Weekly |
| Plasma Viremia | X | X | Daily | Weekly | Daily | Weekly |
| Serum for CD4-IgG Protein | | X | Daily | Weekly | Daily | Weekly |
| DNA-PCR for Both Gene Vectors | | | Daily*** | Weekly | Daily*** | Weekly |
| DNA PCR for HIV DNA | | | | | | |
| Serum for Anti-CD4-IgGAb | | | Day 1 | Weekly | Day 1 | Weekly |
| Serum for Banking | X | X | Day 1 | Weekly | Day 1 | Weekly |

TABLE III-continued

MONITORING DURING THE STUDY

| | Wk 25 | Wks 26-36 | Wk 37 | Wks 38-48 | Wks 48-60 |
|---|---|---|---|---|---|
| Infusion | Day 1 | | Day 1 | | |
| Nursing Visit | Day 1,2 | Weekly | Day 1,2 | Weekly | Q 4 Wks |
| MD Visit | Day 1 | | Day 1 | | Q 4 Wks |
| Performance Status | Day 1,2 | Weekly | Day 1,2 | Weekly | Q 4 Wks |
| CBC Platelet Diff. Retic. | Day 1 | Weekly | Day 1 | Weekly | Q 4 Wks |
| Cong. Profile | Day 1 | Weekly | Day 1 | Weekly | Q 4 Wks |
| Electrolytes | Day 1 | Weekly | Day 1 | Weekly | Q 4 Wks |
| Hepatic. Renal Mineral | Day 1 | Weekly | Day 1 | Weekly | Q 4 Wks |
| Quantiative Immunoglobs. | Day 1 | | Day 1 | | Q 4 Wks |
| Pregnancy Test | Day 1** | | Day 1** | | |
| Hepatitis B, C Screen | | | | | |
| MAI Blood Cultures | | | | | |
| Serum Crypt Antigen | | | | | |
| PPD & Tetanus Control | | | | | |
| Tetanus Toxoid Booster | | | | | |
| Lymphalysis | Day 1 | | Day 1 | | Q 4 Wks |
| Chest X-ray | | | | | |
| ECG | | | | | |
| HIV DNA-PCR | Day 1 | Weekly | Day 1 | Weekly | Q 4 Wks |
| BETA-2-Microglobulin | Day 1 | | Day 1 | | Q 4 Wks |
| Lymphocyte Profile | Daily | Weekly | Daily | Weekly | Q 4 Wks |
| ELISA & Western Blot | | | | | Q 4 Wks |
| Serum p24 Antigen | Daily | Weekly | Daily | Weekly | Q 4 Wks |
| Plasma Viremia | Daily | Weekly | Daily | Weekly | Q 4 WKs |
| Serum for CD4-IgG Protein | Daily | Weekly | Daily | Weekly | Q 4 Wks |
| DNA-PCR for Both Gene Vectors | Daily*** | Weekly | Dsily | Weekly | Q 4 Wks |
| DNA PCR for HIV DNA | | | | | |
| Serum for Anti-CD4-IgGAb | Day 1 | Weekly | Day 1 | Weekly | Q 4 Wks |
| Serum for Banking | Day 1 | Weekly | Day 1 | Weekly | Q 4 Wks |

*The frequency for those tests listed as "daily" or "weekly" may be reduced as the study prcoeeds.
**Pregnancy test results to be obtained prior to infusion and must be negative.
Q and q mean "every."

TABLE IV

Monitoring During The Lymphocyte Infusions

| | PRE-INFUSION | DURING INFUSION | POST-INFUSION |
|---|---|---|---|
| Temperature | X | Q 15 Minutes | Q Hr × 4, then q 4 hr* |
| Blood Pressure | X | Q 15 Minutes | Q Hr × 4, then q 4 hr* |
| Pulse | X | Q 15 Minutes | Q Hr × 4, then q 4 hr* |
| Respiratory Rate | X | Q 15 Minutes | Q Hr × 4, then q 4 hr* |
| Level of Consciousness | X | Q 15 Minutes | Q Hr × 4, then q 4 hr* |
| Subjective Symptonm | X | Q 15 Minutes | Q Hr × 4, then q 4 hr* |
| Oxygen Saturation** (By Pulse Oximetry) | X | Continuous** | Continuous × 4 Hr** |
| Urine Output | | | Q 8 Hours |
| P24 Antigen | X | | |
| Cell Survival Analysis (PCR for Each Vector) | Time 0 (From Bag) | | 5 Min. 1,2,4,5,24 Hrs |
| PCR for HIV DNA | X | | |
| Plasma Viremia | X | | 24 Hrs |

*For the 2nd and 3rd infusions, these parameters will be monitored q 1 hr × 4 only, unless complications occur.
**To be monitored with the 1st infusion only, unless complications occur.
Q and q mean "every".

Although the invention has been described with reference to the presently preferred embodiment, it should be understood that various modifications can be made without departing from the spirit of the invention. Accordingly, the invention is limited only by the following claims.

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:

( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:1:

CACACAACAA GAAGG 15

( 2 ) INFORMATION FOR SEQ ID NO:2:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:2:

TACCAGGTAA TATACCAC 18

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:3:

CAACCAGAGA AACACACGTT 20

( 2 ) INFORMATION FOR SEQ ID NO:4:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:4:

CGGCGGATCC CGGGCGCTTC AGCAAGCCGA 30

( 2 ) INFORMATION FOR SEQ ID NO:5:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO:5:

ACUGGGUCUC UCUGGUUAG 19

( 2 ) INFORMATION FOR SEQ ID NO:6:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:6:

TGCCCGTCTG TTGTGT 16

( 2 ) INFORMATION FOR SEQ ID NO:7:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:7:

TGCCCGTCTG TTATGT 16

( 2 ) INFORMATION FOR SEQ ID NO:8:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:8:

TGCCCGTCTG TTGTGT 16

( 2 ) INFORMATION FOR SEQ ID NO:9:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:9:

TGCCCGTCTG TTGTGT 16

( 2 ) INFORMATION FOR SEQ ID NO:10:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:10:

TGCCCGTCTG TTGTGT 16

( 2 ) INFORMATION FOR SEQ ID NO:11:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:11:

TGCCCGTCTG TTGTGT 16

( 2 ) INFORMATION FOR SEQ ID NO:12:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:12:

TGCCCGTCTG TTGTGT    16

( 2 ) INFORMATION FOR SEQ ID NO:13:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:13:

ACACAACAAG AAGGCAACCA GAGAAACACA CGTTGTGGTA TATTACCTGG TA    52

( 2 ) INFORMATION FOR SEQ ID NO:14:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:14:

CGGCGGATCC CGGGCGCTTC AGCAAGCCGA    30

( 2 ) INFORMATION FOR SEQ ID NO:15:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO:15:

NNNSNGUCNN NNNNNN    16

( 2 ) INFORMATION FOR SEQ ID NO:16:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:16:

TTGGAGTCAG GAACTA    16

( 2 ) INFORMATION FOR SEQ ID NO:17:

( i ) SEQUENCE CHARACTERISTICS:

( A ) LENGTH: 132 base pairs
            ( B ) TYPE: nucleic acid
            ( C ) STRANDEDNESS: single
            ( D ) TOPOLOGY: linear ( i i ) MOLECULE TYPE: DNA ( i x ) FEATURE:
            ( A ) NAME/KEY: -
            ( B ) LOCATION: (96   97)
            ( D ) OTHER INFORMATION: /note="insertion location of
                foreign gene in pol III
                transcription cassette in
                vector pMJT"

( x i ) SEQUENCE DESCRIPTION: SEQ ID NO:17:

| | | | | | |
|---|---|---|---|---|---|
| AAGCTTTGTA | ACCGTTGGTT | TCCGTAGTGT | AGTGGTTATC | ACGTTCGCCT | CACACGCGAA | 60 |
| CGGTCCCCGG | TTCGAAACCG | GGCGGAAACA | GGATCCACGC | GTTTTTGCAT | TTTCTGCAG | 120 |
| GCATGCAAGC | TT | | | | | 132 |

( 2 ) INFORMATION FOR SEQ ID NO:18:

( i ) SEQUENCE CHARACTERISTICS:
            ( A ) LENGTH: 142 base pairs
            ( B ) TYPE: nucleic acid
            ( C ) STRANDEDNESS: single
            ( D ) TOPOLOGY: linear ( i i ) MOLECULE TYPE: DNA ( i x ) FEATURE:
            ( A ) NAME/KEY: -
            ( B ) LOCATION: (106   107)
            ( D ) OTHER INFORMATION: /note="insertion location of
                foreign gene in pol III
                transcription cassette in
                vector pMJV"

( x i ) SEQUENCE DESCRIPTION: SEQ ID NO:18:

| | | | | | |
|---|---|---|---|---|---|
| ATCGATAAGC | TAATTCGAGA | GCCTGTAAGC | GGGCACTCTT | CCGTGGTCTG | GTGGATAAAT | 60 |
| TCGCAAGGGT | ATCATGGCGG | ACGACCGGGG | TTCGAACCCC | GGATCCACGC | GTTTTTGCAT | 120 |
| TTTCTGCAG | GCATGCAAGC | TT | | | | 142 |

What is claimed is:

1. A retroviral vector comprising an infectious retrovirus having inserted between the 5' and 3' long terminal repeat sequences of the retrovirus a nucleic acid sequence encoding a ribozyme which specifically cleaves a human immunodeficiency virus nucleic acid under the control of a pol III promoter.

2. The retroviral vector of claim 1, wherein the ribozyme is a hairpin ribozyme which specifically cleaves an HIV-type 1 virus.

3. The retroviral vector of claim 1, wherein the ribozyme has substantially the same sequence as a ribozyme selected from the group consisting of Rz-1 and Rz-2.

4. The retroviral vector of claim 1, wherein the the ribozyme specifically cleaves an HIV-type 2 virus.

5. The retroviral vector of claim 1, wherein the pol III promoter is selected from the group consisting of the human tRNA$^{Val}$ promoter and the adenovirus VA1 promoter.

6. The retroviral vector of claim 2, wherein the HIV-1 specific ribozyme cleaves the leader sequence of HIV-1.

7. The retroviral vector of claim 1, wherein said vector, when transduced into a human cell, inhibits the replication of HIV nucleic acids in the cell.

8. The retroviral vector of claim 1, wherein said vector comprises more than one ribozyme.

9. The retroviral vector of claim 1, having the capability of transducing a human cell in culture.

10. A pol III promoter transcription cassette selected from the group of transcription cassettes present in the vectors pMJT, pMJV and pMY-2.

11. A host cell stably transformed with the retroviral vector of claim 1.

12. The host cell of claim 11, wherein the host cell is selected from the group consisting of a primate, a murine and a human cell.

13. The host cell of claim 11, wherein the host cell is selected from the group consisting of a fibroblast cell, a CD4$^+$ T cell, a fetal cord blood cell, a peripheral blood lymphocyte cell, a peripheral blood mononuclear cell and a hematopoietic stem cell.

* * * * *